United States Patent [19]
Cerretti et al.

[11] Patent Number: 5,317,087
[45] Date of Patent: May 31, 1994

[54] PURIFICATION OF THE IL-2 RECEPTOR

[75] Inventors: Douglas P. Cerretti; David J. Cosman, both of Seattle; Steven K. Dower, Redmond; Carl J. March, Seattle; David L. Urdal, Seattle; Alf D. Larsen, Seattle, all of Wash.

[73] Assignee: Immunex Corporation, Seattle, Wash.

[21] Appl. No.: 630,331

[22] Filed: Oct. 22, 1990

Related U.S. Application Data

[63] Continuation of Ser. No. 143,277, Jan. 5, 1988, abandoned, which is a continuation of Ser. No. 670,883, Nov. 13, 1984, abandoned.

[51] Int. Cl.$^5$ ............... C07K 13/00; C07K 15/00
[52] U.S. Cl. ................... 530/350; 530/351; 530/395; 435/69.1; 435/69.5; 435/69.52
[58] Field of Search ............... 530/350, 351, 395, 387; 435/69.5, 69.52, 69.1

[56] References Cited

U.S. PATENT DOCUMENTS

| | | |
|---|---|---|
| 4,377,482 | 3/1983 | Rivier . |
| 4,401,756 | 8/1983 | Gillis . |
| 4,411,993 | 10/1983 | Gillis . |
| 4,503,035 | 3/1985 | Pestka et al. ............ 534/351 |
| 4,816,565 | 3/1989 | Honjo et al. ............ 530/351 |

FOREIGN PATENT DOCUMENTS 0091539  10/1983 .

OTHER PUBLICATIONS

Matson et al. *LC-GC*, vol. 4(7) 1986, pp. 624–633.
Deutscher, *Method Enzymology* 182, 1990, pp. 779–780.
A Guide to the Properties and Uses of Detergents in Biology and Biochemistry, 1987, ed Neugebauer, pp. 15–17.
Biochemica Information, 1st ed. ed. Keesey, 1987 pp. 181–198.
Sabe et al, *Mol Biol Med* 1984 (2), pp. 379–396.
Nikaido et al. *Nature* 311, 1984, pp. 631–635.
High Performance Liquid Chromatography of Proteins and Peptides, ed. Hearn et al. 1983 (index only).
Malek et al., *PNAS* 80, 1983, pp. 5694–5698.
Rafh et al., *I. Exp Med* 1981 vol. 154 pp. 1455–1474.
Leonard et al. Nature vol. 300 1982 p. 267.
Aviv and Leder, "Purification of Biologically Active Globin Messenger RNA by Chromatography on Oligo-thymidylic Acid–Cellulose," 69 *Proc. Nat. Acad. Sci. USA* 1408 (1972).
(List continued on next page.)

*Primary Examiner*—Garnette D. Draper
*Attorney, Agent, or Firm*—Foley & Lardner

[57] ABSTRACT

Interleukin-2 receptor derived from normal and malignant cells has been purified by use of various techniques including affinity chromatography in conjunction with a monoclonal antibody directed to the receptor. The purification process also includes reversed phased high performance liquid chromatography. By these techniques, interleukin-2 receptor has been purified to homogeneity. The high purification of the interleukin-2 receptor has made possible the sequencing of the amino acid residues at the N-terminal of this protein molecule. Double-stranded cDNA is prepared from polyadenylated RNA extracted from cell lines or other sources known to produce IL-2 receptor. The cDNA is inserted within a plasmid vector and then the recombinant plasmid employed to transform an appropriate host. Transformed hosts are identified and grouped into pools. Plasmid DNA prepared from these pools is hybridized with a labeled synthetic oligonucleotide probe corresponding to a portion of the amino acid sequence of the purified IL-2 receptor. The cDNA clone isolated with the probe is characterized by restriction enzyme mapping and sequenced by chain-termination method. The particular DNA clone that actually contains the gene coding for the functional IL-2 receptor is identified by expressing the clones in COS-7 monkey kidney cells and assaying for the expressed IL-2 receptor by its ability to bind IL-2 or a monoclonal antibody directed against the IL-2 receptor.

3 Claims, 5 Drawing Sheets

OTHER PUBLICATIONS

Smith and Birnstiel, "A Simple Method for DNA Restriction Site Mapping," 3 *Nucl. Acids Res.* 2387 (1976).

Chirgwin et al., "Isolation of Biologically Active Ribonucleic Acid from Sources Enriched in Ribonuclease," 18 *Biochemistry* 5294 (1979).

Nowinski et al., "The Isolation of Hybrid Cell Lines Producing Monoclonal Antibodies against the p15(E) Protein of Ecotropic Murine Leukemia Viruses," 97 *Virology* III (1979).

Land et al., "5'-Terminal Sequences of Eucaryotic mRNA can be Cloned with High Efficiency," 9 *Nucl. Acids Res.* 2551 (1981).

Robb et al., "T-Cell Growth Factor Receptors. Quantitation, Specificity and Biological Relevance," 154 J. Exp. Med. 1455 (1981).

Uchiyama et al., "A Monoclonal Antibody (Anti-Tac) Reactive With Activated and Functionally Mature Human T-Cells-I. Production of Anti-Tac Monoclonal Antibody and Distribution of Tac (+) Cells," 126 *J. Immunol.* 1393 (1981).

Uchiyama et al., "A Monoclonal Antibody (anti-Tac) Reactive with Activated and Functionally Mature Human T Cells-II. Expression of Tac Antigen on Activated Cytotoxic Killer T Cells, Suppressor Cells, and on One of Two Types of Helper T Cells," 126 *J. Immunol.* 1398 (1981).

Leonard et al., "A Monoclonal Antibody that Appears to Recognize the Receptor of Human T-Cell Growth Factor; Partial Characterization of the Receptor," 300 *Nature (London)* 267 (1982).

Third International Lymphokine Workshop: Interleukins, Lymphokines, and Cyctokines, 70 *Cell Immunol.* 380-407 (1982).

Summary of the Third International Lymphokine Workshop, I *Lymphokine Research*, (1982).

"Studies on Transformation of *Escherichia coli* with Plasmids," 166 *J. Mol. Biol.* 557 (1983).

Robb and Greene, "Direct Demonstration of the Identity of the T Cell Growth Factor Binding Protein and the Tac Antigen," 158 *J. Exp. Med.* 1332 (1983).

Depper et al., "Blockage of the Interleukin-2 Receptor by Anti-Tac Antibody: Inhibition of Human Lymphocyte Activation," 131 *J. Immunol.* 690 (1983).

Leonard et al., "Characterization of the Human Receptor for T-Cell Growth Factor," 80 *Proc. Natl. Acad. Sci. USA* 6957 (1983).

Smith et al., "Production and Characterization of Monoclonal Antibodies to Human Interleukin 2: Strategy and Tactics," 131 *J. Immunol.* 1808 (1983).

```
                                              PstI
                                  5'--CTGCAGGCTTCACTGCCCCGGCTGGTCCCAAGGTCAGGAAG    -2
                                                                                   60
        ↓
Met Asp Ser Tyr Leu Leu Thr Phe Ile Met Val Pro Gly Cys Gln
ATG GAT TCA TAC CTG CTG ACG TTC ATC ATG GTG CCT GGC TGC CAG
     SstI
      *
Ala Glu Leu Cys Asp Asp Pro Pro Glu Ile Pro His Ala Thr Phe Lys Ala Met Ala   19
GCA GAG CTC TGT GAC GAT CCG CCA GAG ATC CCA CAC GCC ACA TTC AAA GCC ATG GCC  120

Tyr Lys Glu Gly Thr Met Leu Asn Cys Glu Cys Lys Arg Gly Phe Arg Arg Ile Lys Ser   39
TAC AAG GAA GGA ACC ATG TTG AAC TGT GAA TGC AAG AGA GGT TTC CGC AGA ATA AAA AGC  180
                             A                A
                             Lys
                                              △
Gly Ser Leu Tyr Met Leu Cys Thr Gly Asn Ser Ser His Ser Ser Trp Asp Asn Gln Cys   59
GGA TCA CTC TAT ATG CTC TGT ACA GGA AAC TCT AGC CAC TCG TCC TGG GAC AAC CAA TGT  240
 G
                                                        △
Gln Cys Thr Ser Ser Ala Thr Arg Asn Thr Thr Lys Gln Val Thr Pro Gln Pro Glu Glu   79
CAA TGC ACA AGC TCT GCC ACT CGG AAC ACA ACA AAA CAA GTG ACA CCT CAA CCT GAA GAA  300

Gln Lys Glu Arg Lys Thr Thr Lys Ile Ile Gln Ser Pro Met Gln Pro Val Asp Gln Ala Ser   99
CAG AAA GAA AGG AAA ACC ACA AAA ATA ATA CAA AGT CCA ATG CAG CCA GTG GAC CAA GCG AGC  360
                                  G   G
                                  Glu Met

```
         PstI
Leu Pro Gly His Cys Arg Glu Pro Trp Glu Asn Glu Pro Pro Ala Thr Glu Arg Ile Tyr 119
CTT CCA GGT CAC TGC AGG GAA CCT TGG GAA AAT GAA CCA CCA GCC ACA GAG AGA ATT TAT 420

His Phe Val Val Gly Gln Met Val Tyr Tyr Gln Cys Val Gln Gly Tyr Arg Ala Leu His 139
CAT TTC GTG GTG GGG CAG ATG GTT TAT TAT CAG TGC GTC CAG GGA TAC AGG GCT CTA CAC 480

Arg Gly Pro Ala Glu Ser Val Cys Lys Met Thr His Gly Lys Thr Arg Trp Thr Gln Pro 159
AGA GGT CCT GCT GAG AGC GTC TGC AAA ATG ACC CAC GGG AAG ACA AGG ACC CAG CCC 540

Gln Leu Ile Cys Thr Gly Glu Met Glu Thr Ser Gln Phe Pro Gly Glu Lys Pro Gln 179
CAG CTC ATA TGC ACA GGT GAA ATG GAG ACC AGT CAG TTT CCA GGT GAA AAG CCT CAG 600
    BglII

Ala Ser Pro Glu Gly Arg Pro Glu Ser Glu Thr Ser Cys Leu Val Thr Thr Thr Asp Phe 199
GCA AGC CCC GAA GGC CGT CCT GAG AGT GAG ACT TCC TGC CTC GTC ACA ACA ACA GAT TTT 660

Gln Ile Gln Thr Glu Met Ala Ala Thr Met Glu Thr Ser Ile Phe Thr Thr Glu Tyr Gln 219
CAA ATA CAG ACA GAA ATG GCT GCA ACC ATG GAG ACG TCC ATA TTT ACA ACA GAG TAC CAG 720

Val Ala Val Ala Gly Cys Val Phe Leu Leu Ile Ser Val Leu Leu Leu Ser Gly Leu Thr 239
GTA GCA GTG GCC GGC TGT GTT TTC CTG CTG ATC AGC GTC CTG CTG CTG AGT GGG CTC ACC 780

XbaI
Trp Gln Arg Arg Gln Arg Lys Ser Arg Arg Thr Ile End                              251
TGG CAG CGG AGA CAG AGG AAG AGT AGA ACA ATC TAG A--3'                             862
```

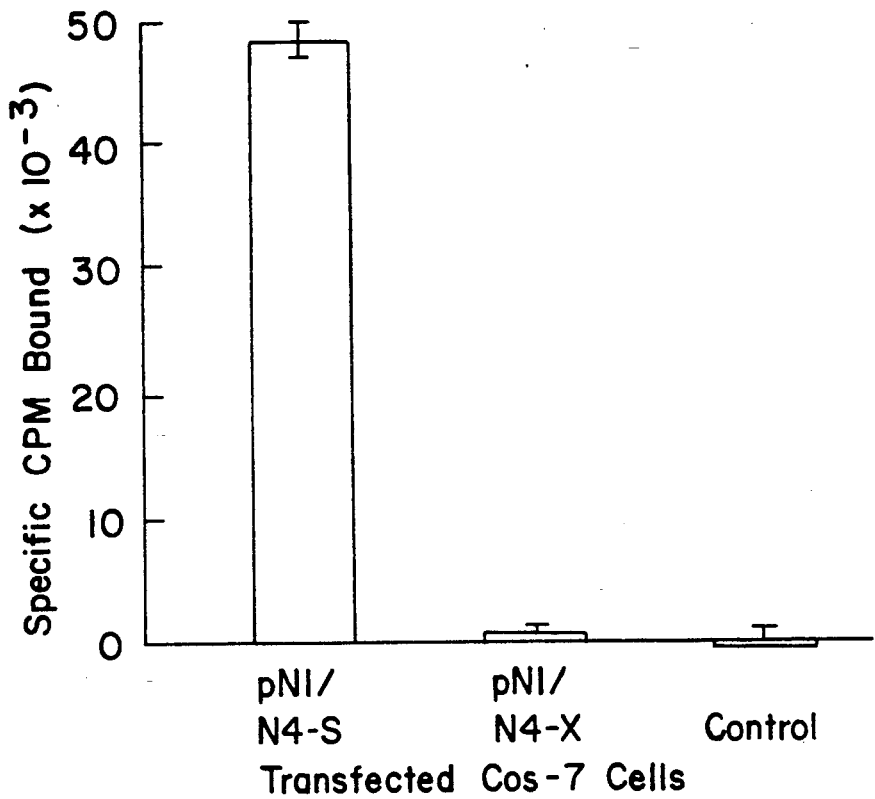
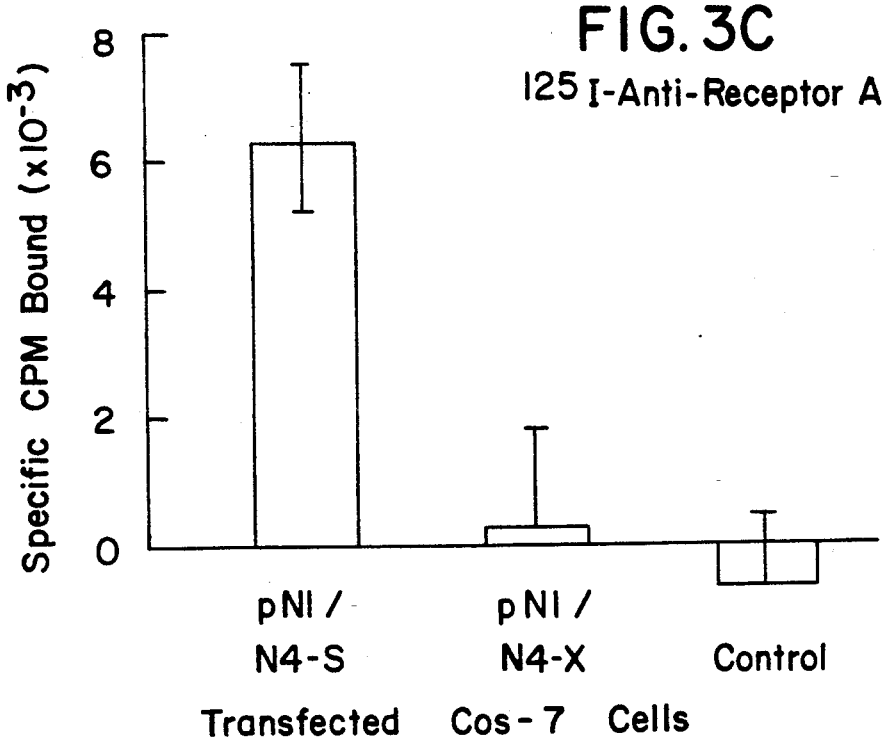

PURIFICATION OF THE IL-2 RECEPTOR

CROSS REFERENCE TO RELATED APPLICATIONS

This application is a continuation of U.S. application Ser. No. 07/143,277, filed Jan. 5, 1988, which, in turn, is a continuation of U.S. application Ser. No. 670,883, filed Nov. 13, 1984, both of which are abandoned.

TECHNICAL FIELD

The present invention relates to interleukin-2 receptor (hereinafter "IL-2 receptor"), and more particularly to: purified interleukin-2 receptor derived from normal and malignant cells; a process for producing same; the cloning of IL-2 receptor gene by use of a synthetic oligonucleotide probe derived from the amino acid sequence of the purified IL-2 receptor to screen a complementary deoxyribonucleic acid ("cDNA") library synthesized from IL-2 receptor messenger ribonucleic acid ("mRNA"); and, the characterization of the screened IL-2 receptor gene.

BACKGROUND OF THE INVENTION

A large number of normal immune responses require the participation of T-cells. The proliferation of T-cells to sufficient numbers to assume an effective role in immune responses is controlled by the presence of interleukin-2 (hereinafter "IL-2"), Gillis and Smith, 28 *Nature* 154 (1977). Although the mechanism by which IL-2 controls the growth of T-cells is not fully understood, it is known that IL-2 acts on T-cells via a specific, high-affinity, plasma membrane receptor, i.e., IL-2 receptor. Also, in order to continue to divide, IL-2 dependent T-cells must express the IL-2 receptor and the IL-2 must bind to a portion of the IL-2 receptor, Robb et al., 154 *J. Exp. Med.* 1455 (1981). A more complete knowledge of the biochemistry of the IL-2 receptor would foster a better understanding of the interaction between IL-2 and T-cells. To date, this has been hampered, at least in part, by the unavailability of sufficient amounts of IL-2 receptor in purified form.

Leonard et al., 300 *Nature (London)* 267 (November 1982), reported employing a murine monoclonal antibody, designated as anti-Tac, to significantly block the binding of radiolabelled IL-2 to the human lymphoma T-cell line, HUT-102. This antibody resulted from the immunization of mice with long term cultures of human T-cells. The anti-Tac antibody was reported as binding both to a glyco-protein having a molecular weight of about 47,000–53,000 daltons and also to proteins having molecular weights of about 113,000 and 180,000 daltons. Leonard et al. hypothesized, but did not establish, that the cell surface determinant (i.e., the 47,000–53,000 molecular weight protein) to which the anti-Tac antibody bounded to was the IL-2 receptor.

Robb and Green, 158 *J. Exp. Med.* 1332 (1983), reported employing the anti-Tac antibody in conjunction with mitogen-activated normal lymphocytes to immunoprecipitate a protein having a molecular weight of about 52,000–57,000 daltons. They found that this same protein also bound to IL-2. These researchers opined that this reactive molecule contained the binding site for IL-2 for normal lymphocytes.

Leonard et al., 80 *Proc. Natl. Acad. Sci. (USA)* 6957 (1983) observed that receptors recognized by anti-Tac antibody on HUT-102 cells and on phytohemaggelutinin-activated normal T-cells appear to be larger on reducing gels than on nonreducing gels, thus suggesting the presence of intrachain disulfide bonds. Also, the HUT-102 cell receptor was reported to exhibit an isoelectric point of from 5.5 to 6.0. From post-translational studies, Leonard et al. suggested that the HUT-102 receptor is composed of a peptide backbone of 33,000 daltons that is initially glycosylated by an N-linked mechanism to achieve a 35,000–37,000 daltons doublet and then glycosylated by an O-linked mechanism to increase the weight of the molecule by about 13,000–15,000 daltons. Although the researchers stated that their studies "suggested" that the HUT-102 cell receptor recognized by the anti-Tac antibody is the human receptor for IL-2, they admitted that actual proof would require purifying the receptor, which prior to the making of the present invention had not been accomplished.

Recombinant DNA techniques have been developed for economically producing a desired protein once the gene coding for protein has been isolated and identified. A discussion of such recombinant DNA techniques for protein production is set forth in the editorial and supporting papers in Vol. 196 of *Science* (April, 1977). However, to take advantage of the recombinant DNA techniques discussed in these references, the gene coding for the IL-2 receptor must first be isolated.

SUMMARY OF THE INVENTION

The present invention relates to the production of IL-2 receptor derived from malignant and normal T-cells, to the purification of the IL-2 receptor to homogeneity and to the determination of the amino acid sequence of the amino terminal portion of the IL-2 receptor molecule. The IL-2 receptor of the present invention is purified by a combination of affinity chromatography and reversed phased high performance liquid chromatography. The affinity chromatography procedure employs a highly specific monoclonal antibody that recognizes an epitope on the receptor molecule.

Once purified to homogeneity, the amino acid sequence of the amino terminal portion of the receptor molecule can be ascertained by use of a protein sequencer. This information is used to construct a hybridization probe to isolate the IL-2 receptor from a cDNA library constructed from mRNA receptors isolated from cells known to express IL-2. To this end, total RNA is extracted from cell lines or other sources known to produce relatively high levels of IL-2 receptor molecules. Polyadenylated mRNA is isolated from the total RNA extract. A cDNA library is constructed by reverse transcription of the polyadenylated mRNA with reverse transcriptase. The DNA is rendered double-stranded with DNA polymerase I and inserted into a cloning vector, and the recombinant vector is used to transform a host.

Transformed hosts are identified and grouped into pools. Plasmid DNA prepared from these pools is hybridized with a labeled synthetic oligonucleotide probe corresponding to a portion of the amino acid sequence of the IL-2 receptor. The pool(s) of clones that give a positive signal to the probe are identified, replated as single colonies, and hybridized with the synthetic oligonucleotide probe to identify the particular host colony containing the IL-2 receptor gene. Plasmid DNA is prepared from this host colony and characterized by restriction enzyme mapping. The IL-2 receptor gene is sequenced to establish its entire nucleotide and amino acid composition. In addition, the IL-2 receptor gene is cloned in a mammalian cell system to express mature IL-2 receptor and then a binding assay is conducted to confirm that the expressed protein product is the IL-2 receptor.

BRIEF DESCRIPTION OF THE DRAWINGS

The details of typical embodiments of the present invention will be described in connection with the accompanying drawings, in which:

FIG. 2 illustrates the nucleotide sequence and the corresponding amino acid sequence of the IL-2 receptor gene as contained in the N4 nucleotide fragment, with the nucleotides being numbered from the position of the initiator methionine codon and the amino acids being numbered from the mature $NH_2$-terminus of the protein, i.e., the Glu residue, as marked with a star;

FIGS. 3B and C illustrate the ability of the transfected mammalian cells to bind to IL-2 and to a monoclonal anti-IL-2 receptor antibody.

DESCRIPTION OF THE INVENTION

Figure 1:
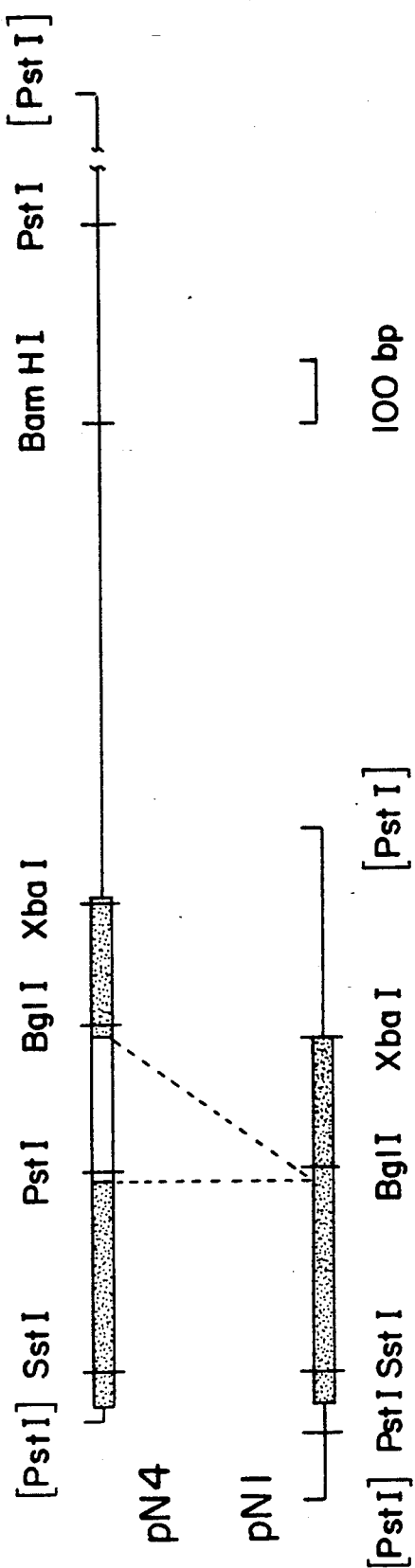
FIG. 1 illustrates partial restriction maps of the IL-2 Rec N4 ("N4") and IL-2 Rec N1 ("N1") clones in side-by-side comparative relationship to each other.

Preparation of IL-2 Receptor Extracts From Malignant and Normal Cells

Malignant cells are cultured in vitro in a suitable culture medium supplemented with serum and various additives. After an optimum culture period, the cells are harvested and IL-2 receptor containing extracts formed from the cells. The malignant cell lines which may be employed as a source of IL-2 receptors include T-lymphoma or T-leukemia cell lines. These cell lines are produced by either a spontaneous occurrence, via viral transformation or via transformation by chemical carcinogen or irradiation. The present invention has been carried out in conjunction with a naturally occurring lymphoma cell line, designated as HUT-102. The cell line is available from a wide variety of sources and has been used extensively by researchers. See, for instance, Leonard et al., 80 *Proc. Natl. Acad. Sci (USA)*, 6957 (1983) and Leonard et al., 300 *Nature (London)*, 267 (November 1982).

The present invention also includes producing IL-2 receptor molecules from normal cells. For instance, human peripheral blood mononuclear cells are separated from human blood by Ficoll-Hypaque centrifugation, such as described by Boyum, 18 *Scand. J. Clin. Lab. Invest. Suppl.* 77 (1966). Adherent cells are removed by plastic adherence and then nonadherent cells are cultured in vitro in serum containing medium in the presence of an activating agent, such as a T-cell mitogen. After a suitable period of time, the cells are harvested by centrifugation. Examples of T-cell mitogens that may be used as activating agents, include phytohemagglutinin ("PHA"), concanavalin A ("Con A") or pokeweed mitogen ("PKM").

The numbers of IL-2 receptors expressed by stimulation of the peripheral blood leukocytes with a plant mitogen varies with time. Optimum levels of IL-2 receptor expression are reached at approximately 72 hours after mitogen stimulation.

The culture medium used to expand the IL-2 receptor bearing malignant and normal cells may consist of commercially available medium, such as Roswell Park Memorial Institute ("RPMI") medium. Dulbecco's Modified Eagle Medium ("DMEM") and Click's Medium. Additives, which may be individually or in combination added to the culture medium, include serum, such as fetal calf serum ("FCS") or normal human serum. Additional additives include glutamine and various antibiotics, such as penicillin and streptomycin.

The process of culturing the malignant and normal cells to induce receptor formation may be carried out in various environmental conditions. Preferably, however, the cultures are maintained in the temperature range of approximately 35°–38° C. in a humidified atmosphere of approximately 5–10% $CO_2$ in air. Also, the pH of the culture should be kept in slightly alkaline condition, in the range of approximately pH 7.0–7.4.

IL-2 receptor containing extracts are prepared from the cultivated normal and malignant cells by harvesting the cells by centrifugation. The cells are then washed with a buffered saline solution and resuspended in the buffered saline solution together with a detergent and phenylmethylsulfonylfluoride ("PMSF"). After a period of time the detergent extract is centrifuged to remove nuclei and insoluble debris and then is stored frozen until used.

Preparation of Monoclonal Antibody Against IL-2 Receptor

The present invention also concerns the production of a monoclonal antibody having a high affinity to an epitope on the IL-2 receptor molecule. The antibody is used as a bound ligand in the affinity chromatography procedures during purification of the IL-2 receptor. The antibody is also employed in a radioimmune precipitation assay and in soluble receptor assays to monitor the IL-2 receptor protein during purification steps, as more fully discussed below.

A preferred procedure for generating the monoclonal antibody against the IL-2 receptor is generally disclosed in U.S. Pat. No. 4,411,993, incorporated herein by reference. In the procedure, BALB/c mice are injected with PHA activated human peripheral blood leukocytes ("PHA/PBL") several times at weekly intervals. Prior to the first injection, the PHA/PBL is emulsified in complete Freund's adjuvant and prior to the remainder of the injections the PHA/PBL is emulsified in incomplete Freund's adjuvant.

During the course of immunization, serum samples from the mice are tested by an enzyme linked immunoabsorbant assay ("ELISA"), as is well known in the art, for the presence of antibody reaction with the immunization cells. Once an antibody titer is detected, the animals are given an intravenous injection of PHA/PBL suspended in saline. Several days later the animals are sacrificed and their spleens harvested. Single cell suspensions from the splenocytes are cultured in tissue culture medium supplemented with various additives to expand the number of antibody producing cells. The antibody producing cells are isolated from the culture and purified by standard techniques for subsequent fusion with myeloma cells to produce hybrid cells that express anti-IL-2 receptor antibody. The fusion process is detailed in U.S. Pat. No. 4,411,933 and in Nowinski et al., 93 *Virology* 111 (1979), incorporated herein by reference.

After fusion, the hybrid cells are resuspended in a tissue culture medium supplemented with various additives and selected suppressing agents to preclude the growth of unfused myeloma cells, double myeloma cells, unfused spleen cells and double spleen cell hybrids, thereby allowing the anti-IL-2 receptor antibody producing cells to grow. Such growth inhibitors or suppressants may include hypoxanthine, aminopterin and thymidine (hereinafter collectively referred to as "HAT").

After several days of culture, the hybridoma cells, which are generated, are screened by ELISA assay for anti-IL-2 receptor antibody responses. These hybrid cells are tested for production of antibody capable of inhibiting both mitogen and antigen induced proliferation of human peripheral blood leukocytes. The hybrid cells which give positive ELISA results are gradually weaned to HAT-free medium and then cultured in vitro in large volumes for bulk production of antibody. Alternatively, the cells may be expanded in vivo by injecting the hybridoma cells in the peritoneal cavities of mice and thereafter collecting the intraperitoneal ascites which contain high concentrations of the antibody. The antibodies contained in the ascites fluid can be isolated and concentrated by established techniques, such as by ammonium sulfate precipitation followed by gel column chromatography. If required, the antibody can be further purified by ion exchange chromatography and/or affinity chromatography. By the above process, a particular hybridoma, designated as 2A3, was found to produce antibody that significantly inhibited both mitogen and antigen induced proliferation of human peripheral blood leukocytes.

The present invention also includes identifying potent cell line sources of anti-IL-2 receptor antibody by cloning cell lines known to produce this antibody, for instance, the 2A3 cell line. The cloning is accomplished by the limiting dilution procedure, as is well known in the art and as is detailed in U.S. Pat. No. 4,411,993. By this procedure, one particular subclone, designated as 2A3-A1H was found to produce antibody that substantially entirely inhibited both mitogen and antigen induced proliferation of human peripheral blood leukocytes. The 2A3-A1H antibody has been characterized as of the $\gamma_1 K$ isotype with an unusually high affinity to the human IL-2 receptor.

A control antibody preferably is employed to confirm the processes of the present invention utilizing anti-IL-2 receptor antibody and as a reagent in the purification of the receptor. The control antibody should be of the same isotype as the anti-IL-2 receptor antibody. Applicants have identified the antibody secreted by the mouse myeloma cell line MOPC-21 as a suitable control antibody for the 2A3-A1H antibody. The MOPC-21 cell line is widely available from numerous private and commercial sources.

Soluble IL-2 Receptor Assays

Assays employing the 2A3-A1H monoclonal antibody are used in conjunction with the present invention to monitor the quantitative amount of IL-2 receptor present in the initial cell lysates and during purification procedures. These assays hinge on the discovery by applicants that the 2A3-A1H antibody has an extremely high affinity for the IL-2 receptor, the affinity constant being in excess of $5 \times 10^9 M^{-1}$ and that the 2A3-A1H antibody can be radioiodinated to high specific activity and still retain its capacity to bind to the IL-2 receptor.

One such preferred assay involves ascertaining the extent to which samples of cell lysate or column chromatography fractions containing IL-2 receptors are capable of inhibiting the binding of radiolabelled IL-2 antibody to glutaraldehyde fixed, intact receptor bearing cells. This assay relies on the observation by applicants that IL-2 receptor is stable to glutaraldehyde fixation, i.e., the receptor cannot be extracted from such cells with nonionic detergents, such as Triton X-100, and the presence of detergent does not affect the binding of radiolabelled 2A3-A1H antibody to the fixed cells. Preincubation of a subsaturating dose of iodinated 2A3-A1H antibody with detergent solutions containing the IL-2 receptor inhibits the subsequent binding of the 2A3-A1H antibody to the glutaraldehyde fixed cells. This assay will hereinafter be referred to as the "soluble inhibition assay."

For use in the soluble inhibition assay, the 2A3-A1H antibody is radiolabeled with iodine 125 ("$^{125}I$") by a chloramine-T method, as is well known in the art and as described by Segal and Hurwitz, 118 *J. Immunol.* 1338 (1977). The standard labeling conditions employed are: 50 micrograms ("ug") 2A3-A1H IgG; 4 nanomoles ("nM") of chloramine-T (Sigma Chemical Company, St. Louis, Mo.); and, 2.5 microcurins ("mCi") of $^{125}I$ sodium iodide (New England Nuclear, Boston, Mass.), in a final volume of 60 microliters ("ul"). This protocol has resulted in preparations of $^{125}I$-2A3-A1H, which routinely have specific activities in the range of 2 to $5 \times 10^{15}$ counts per minute/millimole ("cpm/mMol") ($1.3-3.3 \times 10^7$ cpm/ug). Also, 2A3-A1H antibodies labeled in this way were found to be more than 95 percent bindable to IL-2 receptor bearing cells and had apparent affinity constants in excess of $5 \times 10^9 M^{-1}$.

In the soluble inhibition assay, 50 ul of $^{125}I$-2A3-A1H [($2 \times 10^{-10}M$ in RPMI-1640 medium containing 2% bovine serum albumin ("BSA"), 20 mM HEPES buffer (pH 2.7) and 0.2% sodium azide ("$NaN_3$") (collectively "binding medium")] is mixed with 50 ul of cell lysate or column fraction diluted in phosphate buffered saline ("PBS") containing 1% (w/v) Triton X-100 detergent (Sigma Chemical Company, St. Louis, Mo.). This mixture is incubated for one hour at room temperature in round bottom 96 well plates (Linbro, Hamden, Conn.). At the end of the incubation period, $10^7$ glutaraldehyde fixed, PHA activated human T-cells in 50 ul of binding medium are added to detect uncomplexed $^{125}I$-2A3-A1H. Incubation is continued for one hour at room temperature. Duplicate 60 ul aliquots of the mixture are then transferred to precooled 400 ul polyethylene centrifuge tubes containing 200 ul of a phthalate oil mixture and the cell bound antibody is separated from unbound antibody by centrifugation. The details of the well-known phthalate oil separation method are set forth in Segal and Hurwitz, supra. The percent of specific inhibition caused by the lysate or column fraction is calculated by using 50 ul of PBS-2% Triton X-100 instead of a test sample for the positive control. Also, 15 ul of PBS-2% Triton X-100 containing $10^{-8}M$ unlabeled 2A3-A1H is used as a negative control.

The nitrocellulose dot assay ("dot assay") is used as a second soluble IL-2 receptor assay to quantify the amount of IL-2 receptor molecules present in a sample of cell lysate or column fraction. Briefly, in the dot assay, solutions are made of a $log_2$ dilution series of potential IL-2 receptor containing samples and PBS containing 1% Triton X-100. Samples of 5 ul of these solutions are then applied to a piece of dry nitrocellulose (Schleicher and Schuell, Keene, N.H.). The nitrocellulose is then blocked by overnight incubation in 10 ml of 0.5 M TRIS, (pH 7.5), 0.15M NaCl, 3% BSA (hereinafter TBS-3% BSA). After the blocking step, the nitrocellulose is incubated for one hour at room temperature in 10 ml of TBS-3% BSA containing 0.05 ug/ml $^{125}$I-2A3-A1H and 0.6 ug/ml unlabeled MOPC-21. The nitrocellulose is then washed three times in TRIS buffered saline and twice in TRIS buffered saline containing 1% (w/v) Nonidet P-40 detergent (Gallard Schlesinger Chemical Manufacturing Corp., Carle Place N.Y.), 1% (w/v) sodium deoxycholate, and 0.1% (w/v) sodium lauryl sulfate. Each of these washes lasts 30 minutes at room temperature. After the final wash, the nitrocellulose sheet is blotted dry, covered with a clear plastic sheet and then exposed at $-70°$ C. to Kodak X-omat AR ® film.

Radioimmune Precipitation Assay

The specificity of the IL-2 receptor antibody is ascertained with a radioimmune precipitation assay involving forming precipitations between samples of radiolabeled IL-2 receptor molecules and an antibody to the receptor and then employing polyacrylamide gel electrophoresis and either fluorography or autoradiography to visualize the receptor proteins that were precipitated. In this assay technique, the IL-2 receptor molecules are labeled either by surface iodination metabolically before extraction.

A surface podination of the IL-2 receptor on cell membranes after extraction is performed by the $^{125}$I-IODO-GEN method (Pierce Cl. Co., Rockford, Ill.). The details of this radiolabeling technique are well known in the art and described by Urdal et al., 1 Cancer Metastasis Reviews 65 (1982); and, Markwell et al., 17 Biochemistry (Wash.) 4807 (1978). The use of $^{35}$S methionine to label the receptor molecules metabolically also is well known in the art and is described by, for instance, Robb and Greene, supra.

After labeling with $^{125}$I or $^{35}$S methionine, the cells are washed with PBS and then extracted with PBS containing 1% Triton X-100 and 2 mM PMSF. Affinity supports for the radioimmune precipitation assay are prepared by coupling purified antibodies (2A3-A1H and MOPC-21) to Affi-gel-10. Briefly, one volume of moist Affi-gel-10 is added to one volume of antibody (3-5 mg/ml) in borate buffered saline ("BBS") and then the mixture incubated overnight at 4° C. Thereafter, 100 ul of 1M glycine ethylester is added per ml of gel to couple any of the unreacted groups on the Affi-gel-10. Applicants have found that routinely from 3 to 4 mg of antibody are coupled per ml of the gel under these conditions. Before use, each gel is washed extensively with PBS. Each gel is also washed with a buffer solution composed of PBS-1% Triton X-100 and 0.5 M TRIS, pH 7.5, containing 0.5M NaCl, 1% (w/v) NP 40 detergent, 1% (w/v) sodium deoxycholate, and 0.1% sodium dodecyl sulfate ("SDS") (collectively "RIPA buffer").

The radioimmune precipitations are performed by mixing 50 ul of radiolabeled cell extract with 75 ul of PBS-1% percent Triton X-100 containing 20% (v/v) of affinity gel having antibody coupled thereto. The mixture is incubated over night at 4° C. and then the gel washed four times with RIPA buffer and twice with 0.1M TRIS, pH 8.0, containing 0.5M NaCl, 5 mM, ethylene diamine tetra acetate ("EDTA"), and 0.5% NP-40 detergent. After the final wash, the resulting gel pellets are suspended in 40 ul of SDS polyacrylamide gel sample buffer (0.06M TRIS, pH 6.8, 2% SDS, 10% glycerol, 5% 2-mercaptoethanol and boiled for three minutes to break apart the bonds between the antibody and the IL-2 receptor molecules. A 30 ul sample of the supernate is then analyzed by SDS-polyacrylamide gel electrophoresis (PAGE) (8-12% polyacrylamide gel for $^{125}$I labeled receptor; 12% polyacrylamide gel for $^{35}$S methionine labeled receptor) according to the stacking gel procedure of Laemmli, 227 Nature (London) 680 (1970).

In the lysate analysis the receptor proteins employing the $^{35}$S methionine gels are visualized by fluorography. To this end, the $^{35}$S methionine gels were impregnated with Enhance (New England Nuclear, Boston, Mass.) prior to drying and fluorography. The receptor proteins immunoprecipitated with the $^{125}$I gels are visualized by autoradiography. To this end, the $^{125}$I gels are stained with Coomassie blue prior to drying and autioradiography. Both the $^{35}$S methionine and $^{125}$I gels are exposed to Kodak X-omat AR ® film at $-70°$ C. for 24 to 72 hours.

Gel Electrophoresis of Chromatography Column Fractions

Fractions eluted from the affinity chromatography and reversed phase HPLC columns employed in the purification processes of the present invention are assayed by gel electrophoresis. 50 ul aliquots are removed from the eluate fractions. The aliquots are dried under vacuum after addition of 2 ul of 10% SDS (w/v) to each aliquot. The dried residue is dissolved in 40 ul of SDS polyacrylamide gel sample buffer and then boiled for 3 minutes. The solution is applied to an 8% polyacrylamide gel and electrophoresis is then carried out by the stacking gel procedure of Laemmli, supra. The resulting gel samples are silver stained by the method described by Oakley et al., 105 Anal. Biochem. 361 (1980).

Purification of IL-2 Receptor

Cell extracts from the malignant and normal cells produced by the above procedures are initially concentrated by affinity chromatography techniques employing the same affinity supports used in the radioimmune precipitation assay described above. The procedure employed involves applying cell extracts first to an MOPC-21 column and then to a second column prepared with a mixture of MOPC-21 antibody and 2A3-A1H antibody so that in the second column from 3 to 4 mg of total IgG is coupled to each ml of gel, but only 10 to 30% of the antibody is composed of 2A3-A1H. This technique is used to counteract the extremely high affinity between the 2A3-A1H antibody and the IL-2 receptor.

In the purification procedure, the cell extracts, as prepared above, are first applied to the MOPC-21 column that has been preequilabrated with a buffer containing a detergent, thereby to remove proteins in the cell extract that might nonspecifically bind to mouse immunoglobulin. The flow through from the MOPC-21 column is then applied to the 2A3-A1H column. Elution from this column is carried out with a guanidine-HCL detergent solution. The recovered fractions are then dialyzed against decreasing concentrations of the eluting agent to optimize the recovery of biological activity.

Fractions are collected and assayed by gel electrophoresis and silver staining, as described above. Applicants have found that by use of the affinity chromatography procedure, IL-2 receptor from malignant cells which constitutively produce the receptor is purified approximately 1600 times from initial cell lysate. A somewhat lower purification level is typically attained for IL-2 receptor from activated normal cells.

The pooled active fractions from the above affinity chromatography procedure is employed as a starting material for the HPLC procedures. The HPLC technique used in the present invention preferably employs a reversed phase, tetra methyl bonded silica column having a pore size sufficiently large to be optimumly utilized with the proteineaceous IL-2 receptor, i.e., a pore size of at least 300 Å.

Suitable reversed phased HPLC columns for use in the practice of the present invention are articles of commerce. A preferred column for this purpose is the Vydac C-4 reversed phase column commercially available from Separations Group, Hesperia, Calif. This column consists of tetra methyl silane groups covalently bonded by means of a siloxane (silicon-oxygen-silicon) bond to the surface of the 300 Å pore diameter silica gel which has been classified to a mean particle size of 5 microns. Alternative HPLC columns which may be employed in the present invention include those constructed with octylsilane (Vydac C-8) or octyldecylsilane (Vydac C-18) resins covalently bonded to silica gel.

The elution of the proteins from the HPLC column is carried out in a manner well known in the art. A suitable elution procedure for removing the bonded receptor molecule proteins from the tetra methyl column involves the use of a linear gradient of acetonitrile. A preferred gradient for this purpose is 0 to 95 percent (v/v) acetonitrile gradient in 0.1% (v/v) trifluoroacetic acid (TFA), pH 2.1.

The eluted protein can be conveniently monitored with detection systems that are well known in the art. The relative protein concentration in the fractions eluted from the HPLC columns can be determined by measuring absorbance of the eluded material in an automated ultraviolet light spectrophotometer, at 214 nanometers light wave length. The suitable automated ultraviolet light absorbance detection apparatus is available from Waters Associates, Millford, Mass. Final identification of the IL-2 receptor is dependent on the detection of the receptor by use of the soluble receptor assay and by use of gel electrophoresis as described above.

By use of the above-described soluble receptor assay techniques, applicants have found that the specific activity of the IL-2 receptor after HPLC purification is very high, i.e., approximately 21,000 fmole IL-2 receptor/ug protein for IL-2 receptor derived from malignant cells. This is approximately a 16,700 fold level of purification over the specific activity of the IL-2 receptor in the starting cell lysate. The specific activity of the IL-2 receptor from normal T-cells was about ½ of the specific activity from malignant cells. By polyacrylamide gel electrophoresis and silver staining, applicants ascertained that the molecular weight of the IL-2 receptor from normal cells is approximately 60,000 daltons, as opposed to 55,000 daltons for receptor molecules found constitutively on the malignant cells.

Amino Acid Sequencing

The ability to prepare homogeneous IL-2 receptor has permitted applicants to determine the amino acid sequence of the amino terminal portion of this molecule. This information may be employed to assist in the cloning of the IL-2 receptor gene and the production of large quantities of pure IL-2 receptor for clinical trials and ultimately for widespread medical use. Moreover, the availability of homogeneous IL-2 receptor will no doubt lead to a more complete understanding of the biology of IL-2. While the prior art has said to have partially "characterized" the IL-2 receptor, applicants are not aware of any instances in which this protein has been truly purified to homogeneity to the extent that the receptor can be analyzed for amino acid composition and sequence.

Samples of homogeneous IL-2 receptor, as prepared above, can be analyzed for amino acid composition and sequence, for instance with an automated sequencer, such as with an Applied Biosystems model 470A protein sequencer. Ideally, several sequencing runs are made to confirm the accuracy of the sequence. Through this technique, applicants have found that the first 15 residues of the amino terminal portion of the IL-2 receptor molecule are composed of the following sequence: Glu-Leu-Cys-Asp-Asp-Asp-Pro-Pro-Glu-Ile-Pro-His-Ala-Thr-Phe.

Sources of IL-2 Receptor Producing Cells

Preferably, a cDNA library, from which the gene coding for the IL-2 receptor will be sought, is constructed from cells known to produce high levels of IL-2 receptor. As noted above, these sources may include malignant cell lines that have previously been identified as high level IL-2 receptor producers, such as the human lymphoma T-cell line designated as HUT-102, and human peripheral blood mononuclear cells.

Preparation of RNA from IL-2 Receptor Bearing Cells

Total RNA from the IL-2 receptor bearing cells is extracted by standard methods, such as disclosed by Chirgwin et al., 18 *Biochemistry* 5294 (1979) and Maniatis et al., *Molecular Cloning, a Laboratory Manual*, Cold Spring Harbor Laboratory, Cold Spring Harbor, N.Y. (1982).

As is well known, when extracting RNA from cells, it is important to minimize ribonuclease ("RNase") activity during the initial stages of extraction. One manner in which this is accomplished is to denature the cellular protein, including the RNase, at a rate that exceeds the rate of RNA hydrolysis by RNase. In the procedures of Chirgwin et al., supra, and Maniatis et al., supra at 196, this is carried out by use of guanidinium thiocyanate, together with a reducing agent, such as 2-mercaptoethanol (to break up the protein disulfide bonds). The RNA is isolated from the protein by standard techniques, such as phenol/chloroform extraction, ethanol precipitation or sedimentation through cesium chloride.

Although several techniques have been developed to separate the polyadenylated mRNA from the extracted protein, one preferred method is to chromatograph the polyadenylated mRNA on oligo (dT)-cellulose in the well known manner described by, for instance, Edmonds et al., 68 *Proc. Natl. Acad. Sci. (USA)* 1336 (1971); Aviv and Leder, 69 *Proc. Natl. Acad. Sci. (USA)* 1408 (1972); and Maniatis et al., supra at 197. The oligo (dT)-cellulose column is prepared with a loading buffer and then the mRNA applied to the column. Thereafter, the column is initially washed with a buffer solution to remove the unpolyadenylated mRNA and then the polyadenylated mRNA is eluted from the column with a buffered, low ionic strength, eluent. The integrity of the polyadenylated mRNA is verified by gel electrophoresis.

Preparation of cDNA from mRNA

A library of double-stranded cDNA corresponding to the mRNA is prepared by known techniques employing the enzyme reverse transcriptase. One such procedure which may be employed in conjunction with the present invention is detailed by Maniatis et al., supra at 230. Briefly, the polyadenylated mRNA is reverse transcribed by using oligo-dT that has been hybridized to the polyadenylated tail of the mRNA, as a primer for a first cDNA strand. This results in a "hairpin" loop at the 3' end of the initial cDNA strand that serves as an integral primer for the second DNA strand. Next, the second cDNA strand is synthesized using the enzyme DNA polymerase I and the hairpin loop is cleaved by S1 nuclease to produce double-stranded cDNA molecules. The double-stranded cDNA is fractionated by any convenient means to remove the shorter strands thereby avoiding the needless cloning of small cDNA fractions.

It is to be understood that in accordance with the present invention, alternative well known procedures may be employed to prepare double-stranded cDNA from mRNA. One such alternative technique is disclosed by Land et al., 9 *Nucl. Acids Res.* 2251 (1981). In the Land et al. protocol, the hairpin loop is not used as a primer for the second cDNA strand. Rather, the 3' end of the first cDNA strand is tailed with dCMP residues using terminal deoxynucleotidyl transferase ("TdT"). This produces a 3' tail of poly-C residues. Then the synthesis of the second strand is primed by oligo-dG hybridized to the 3' tail. This technique is said to help avoid losing portions of the 5' tail of the second cDNA strand which might occur if the hairpin is cleaved with S1 nuclease, as in the Maniatis et al. protocol.

Cloning of cDNA

Next, the double-stranded cDNA is inserted within a cloning vector which is used to transform compatible prokaryotic or eukaryotic host cells for replication of the vector. Thereafter, the transformants are identified and plasmid DNA prepared therefrom.

To carry out the present invention, various cloning vectors may be utilized to clone the cDNA. Although the preference is for a plasmid, the vector may be a bacteriophage or a cosmid. If cloning occurs in mammalian cells, viruses also can be used as vectors.

If a plasmid is employed, it may be obtained from a natural source or artificially synthesized. The particular plasmid chosen should be compatible with the contemplated transformation host, whether a bacteria such as Escherichia coli ("*E. coli*"), yeast, or other unicellular microorganisms. The plasmid should have the proper origin of replication for the particular host cell to be employed. Also, the plasmid should have a phenotypic property that will enable the transformed host cells to be readily identified and separated from cells that do not undergo transformation. Such phenotypic characteristics can include genes providing resistance to growth inhibiting substances, such as an antibiotic. Plasmids are widely available that encode genes resistant to various antibiotics, such as tetracycline, streptomycin, sulfa drugs, penicillin, and ampicillin.

If *E. coli* is employed as the host cell, many possible cloning plasmids are commercially available which may be used in conjunction with the present invention. A preferred plasmid for performing the present invention is pBR322. This plasmid is widely commercially available and has been fully sequenced, as set forth in Sutcliffe, 43 *Cold Spring Harbor Symp. Quant. Biol.* 77 (1979). A significant advantage of this plasmid is that it has 11 known unique restriction sites at which the plasmid may be cleaved by a specific enzyme, including the Pst I site in the ampicillin resistant gene. This feature is particularly useful for cloning by the homopolymer tailing method.

If a bacteriophage is used instead of a plasmid, such phages should have substantially the same characteristics noted above for selection of plasmids. This includes the existence of a phenotypic marker and ligatable termini for attachment of foreign genes.

The double-stranded cDNA prepared from mRNA, having blunt ends, may be inserted within a plasmid cloning vector by various methods that are well-known in the art. One such technique involves attaching linkers to the ends of the cDNA strands. The linkers are composed of approximately 8 to 10 base pair oligonucleotides that are synthesized chemically and added to the double-stranded cDNA by using DNA ligase. The linkers are then cleaved with a restriction enzyme to generate cohesive termini for insertion within a plasmid cleaved with the same restriction enzyme.

An alternative procedure, and of preference in the present invention, is to insert the double-stranded cDNA into a plasmid vector by homopolymeric tailing. In this technique, complementary homopolymer tracks are added to the strands of the cDNA and to the plasmid DNA. The vector and double-stranded cDNA are then joined together by hydrogen bonding between complementary homopolymeric tails to form open, circular hybrid molecules capable of transforming host cells, such as *E. coli*.

In one procedure for homopolymeric tailing, approximately 50 to 150 dA nucleotide residues are added to the 3' ends of linearized plasmid DNA. A similar number of dT nucleotide residues are added to the 3' ends of the double-stranded cDNA and then the cDNA and plasmid joined together.

In an alternative tailing method, dG tails are added to the 3' ends of the cloning vector that has been cleaved with an appropriate restriction enzyme. For instance, if the pBR322 plasmid is employed, the restriction enzyme Pst I may be used to digest the plasmid at the ampicillin resistant gene. Complementary dC tails are added to the 3' ends of the double-stranded cDNA prior to insertion of the cDNA segment in the plasmid with an appropriate annealing buffer.

The recombinant DNA plasmids, as prepared above, are used to transform host cells. Although the host may be any appropriate prokaryotic or eukaryotic cell, preferably, it is a well-defined bacteria, such as *E. coli* or a yeast strain. Such hosts are readily transformed and capable of rapid growth in culture. However, in place of *E. coli*, other unicellular microorganisms may be employed, for instance, fungi and algae. In addition, various forms of bacteria, such as salmonella or pneumococcus may be substituted for *E. coli*. Whatever host is chosen, it should not contain a restriction enzyme that would cleave the recombinant plasmid.

If *E. coli* is employed as a host, a preferable strain is MM294. Protocols for transformation of this particular host by a plasmid vector are well known, for instance, see Maniatis et al., supra at 255; and, Hanahan, 166 *J. Mol. Biol.* 557 (1983). Other strains of *E. coli* which also could serve as suitable hosts include RR1, DH1 (ATCC No. 33849) and C600. These strains and the MM294 strain are widely commercially available.

During transformation, only a small portion of the host cells are actually transformed, due to limited plasmid uptake by the cells. The cells that have been transformed can be identified by placing the cell culture on agar plates containing suitable growth medium and a phenotypic identifier, such as an antibiotic. Only those cells that have the proper resistance gene (e.g., to the antibiotic) will survive. If the recombinant pBR322 plasmid is used to transform *E. coli* strain MM294, transformed cells can be identified by using tetracycline as the phenotypic identifier.

Preparation of a Synthetic Oligonucleotide Screening Probe

A radiolabeled synthetic oligonucleotide corresponding to a portion of the amino acid sequence of the IL-2 receptor, as determined above, is used as a probe to screen the cDNA library. The hybridization of the synthetic oligonucleotide probe with plasmid cDNA prepared from the library clones is subsequently identified by autoradiography.

The amino terminal portion of the IL-2 receptor molecule has been identified and partially sequenced, above. A portion of this amino acid sequence, composed of the residues: Cys-Asp-Asp-Asp-Pro-Pro, is employed as the basis for the synthetic oligonucleotide probe. This particular portion of the amino acid sequence of the IL-2 receptor has the advantage of being short enough to be easily chemically synthesized, while also being long enough to be useful as a direct probe for the IL-2 receptor gene. Also, this sequence corresponds to a particular codon composition that is relatively free of ambiguity.

Applicants have developed two synthetic oligonucleotides from the above amino acid sequence for use as probes to screen plasmid DNA thought to contain the IL-2 receptor genes. The probes are composed of the following two sequences each having 17 bases: 5' G-G-$C^T$-G-G-G-T-C-G-T-C-G-T-C-A-C-A 3'. The particular compositions of these probes were arrived at after conducting initial primer extension analysis which enabled applicants to eliminate other possible oligonucleotide sequences corresponding to the above-identified amino acid sequence. The compositions of the probes are the same except for the third nucleotide from the 5' end, which in one oligonucleotide is composed of thymidine and in the other is composed of cytosine. Also, the last nucleotide of Pro residue was not employed thereby to reduce the ambiguity of the oligonucleotide probes.

Although the described oligonucleotide sequences are the preferred composition of the synthetic probes of the present invention, it is to be understood that probes of other compositions corresponding to additional partial amino acid sequences of the IL-2 receptor molecule can be employed without departing from the spirit or scope of the present invention.

The synthetic oligonucleotide probes may be chemically synthesized by well-known techniques, such as by phosphodiester or triester methods. Methods for triester synthesis are set forth in Sood et al., 4 *Nucl. Acid Res.* 2557 (1977); and, Hirose et al., 28 *Tet. Lett.* 2449 (1978). After synthesis, the oligonucleotide probe is labeled with T4 polynucleotide kinase and $^{32}$P-ATP, for instance by the protocol set forth in Maniatis et al., supra at 122. Advantageously, the oligonucleotide probes can be synthesized with OH 5' termini thereby avoiding the phosphatase procedure typically required.

Screening of cDNA Library

In the screening procedure of the present invention, the transformed bacteria cultures are pooled into groups. After the replicated plasmids have been extracted from the transformants, DNA is prepared by cleaving the plasmids at the Pvu II and Hind III restriction sites, both being unique sites on the hybrid plasmid. The resulting DNA segments are fractionated by electrophoresis on agarose gels and then directly analyzed by Southern blotting, for instance as described in 98 *J. Mol. Biol.* 503 (1975). The DNA that binds to the nitrocellulose filter in the Southern blotting procedure is hybridized with the labeled oligonucleotide probes. The specific DNA fragments that hybridize to the probe are identified by autoradiography.

The particular pool(s) of clones that give a signal following autoradiography are plated out and used in direct bacterial colony hybridization on a nitrocellulose filter with the same above-identified oligonucleotide probes. After completion of the hybridization, the nitrocellulose filter is monitored by autoradiography to identify positive colonies. In the present invention, applicants discovered two such positive colonies. Plasmid DNA, designated as IL-2 Rec N4 (hereinafter "N4") and IL-2 Rec N1 (hereinafter "N1") were prepared from the two particular positive colonies identified.

Characterization of Screened cDNA

The plasmid DNA prepared above is initially characterized by restriction enzyme mapping. Various strategies for restriction enzyme mapping are discussed by Maniatis et al., supra at 374. One preferred technique involves the partial digestion of end-labeled fragments of linear DNA. This technique, developed by Smith and Birnstiel, 3 *Nucl. Acids Res.* 2387 (1976), is now well known in the art. Partial restriction enzyme maps of the N4 cDNA clone in the region of the IL-2 receptro gene and of the N1 cDNA clone are shown in FIG. 1. A distance scale for 100 nucleotide base pairs ("bp") is also shown. The Pst I sites shown in brackets are those generated by the cloning procedures.

The mapped plasmid cDNAs are initially partially sequenced to determine whether they are homologous to the amino acid sequence of the IL-2 receptor. Although applicants have ascertained that both cDNA clones illustrated have nucleotide sequences corresponding to the known N-terminus amino acid sequence of the IL-2 receptor, as discussed below, only the pN4 cDNA clone contains the gene coding for IL-2 receptor. The N-terminus of the mature IL-2 receptor protein is located at the Sst I site of the N4 clone.

Thereafter, the cloned cDNA's are sequenced using chain-termination method. This method of nucleotide sequencing was originated by Sanger et al., 70 *Proc. Natl. Acad. Sci. (USA)* 5463 (1977). See U.S. Pat. No. 4,322,499. Methods for chain-termination sequence determination are set forth in the Amersham Handbook entitled, *M13 Cloning and Sequencing*, Blenheim Cresent, London (1983) (hereinafter "Amersham Handbook"); Messing, 2 *Recombinant DNA Technical Bulletin, NIH Publication No.* 79–99, 2, 43–48 (1979); Norrander et al., 26 *Gene* 101 (1983); Cerretti et al., 11 *Nucl. Acids Res.* 2599 (1983); and, Biggin et al., 80 *Proc. Natl. Acad. Sci.* (*USA*) 3963 (1983). M13 filamentous phage are employed as vectors to clone the DNA sequences of interest. These phage vectors provide single-stranded DNA templates which are readily sequenced by chain-termination method, which involves priming a single-stranded template molecule with a short primer strand having a free 3' hydroxyl group and then using DNA polymerase to copy the template strand in a chain extension reaction using all four deoxyribonucleotide triphosphates, i.e., dATP, dCTP, dGTP, and dTTP (collectively referred to as "dNTPs"), with one of them being radiolabeled. In the synthesis reaction, a nucleotide specific chain terminator lacking a 3'-hydroxyl terminus, for instance, a 2', 3' dideoxynucleotide triphosphate ("ddNTP"), is used to produce a series of different length chain extensions. The terminator has a normal 5' terminus so that it can be incorporated into a growing DNA chain, but lacks a 3' hydroxyl terminus. Once the terminator has been integrated into the DNA chain, no further deoxynucleotide triphosphates can be added so that growth of the chain stops. Four separate synthesizing reactions are carried out, each having a ddNTP of one of the four nucleotide dNTPTs, i.e., dATP, dCPT, dGTP and dTTP. One of the normal dNTPs is radiolabeled so that the synthesized strands after having been sorted by size on a polyacrylamide gel, can be autoradiographed. The chain extensions from the four reactions are placed side by side in separate gel lanes so that the pattern of the fragments from the autoradiography corresponds to the DNA sequence of the cloned DNA.

The DNA and corresponding amino acid sequences of the N4 and N1 clones from the 5' ends to the Xba I restriction site, as determined by the above techniques, are illustrated in FIG. 2. As detailed below, the gene coding for IL-2 receptor is contained in the N4 clone and not in the N1 clone. In FIG. 2, the nucleotide sequence shown is from the N4 clone except for the sequences upstream from the arrow, which are derived from the N1 clone. The arrow marks the 5' end of the insert in the N4 clone. The nucleotides are numbered from the position of the initiator methionine codon to the TAG termination codon. The amino acids are numbered beginning from the mature NH2-terminus of the IL-2 receptor protein, i.e., the Glu residue, marked with a star, and extending to the Ile residue (251) located adjacent the termination codon TAG. The IL-2 receptor gene, extending from the initiator methionine codon to the TAG termination codon, is shown as a box portion in FIG. 1. Correspondingly, the coding region of the N1 clone is shown as a box portion. The restriction enzyme cleaving sites identified in FIG. 1 are also indicated in FIG. 2.

The base sequence of the N1 clone differs from the N4 clone, in that the N4 clone contains a 216 base pair insert sequence not present in the N1 clone, extending from nucleotides 370 to 585 (underlined in dots in FIG. 2). This 216 base pair insert is shown in FIG. 1 as the unshaded box portion of the N4 clone. The two clones also differ at nucleotides 148, 183, 322 and 327. In addition, as shown in FIG. 2, three of these sequence differentials would cause amino acid changes. In terms of similarities, both clones contain the sequence of the oligonucleotide probe employed above, with a single base pair mismatch, and both encode the amino acid sequence determined above for the NH2-terminus of the IL-2 receptor. Both also encode a stretch of 15 amino acids immediately preceding the NH2-terminus sequence, which starts with a methionine residue and has many of the characteristics of a hydrophobic signal peptide expected from membrane or secreted proteins.

In preparation for the sequencing procedures, the cDNA clones shown in FIG. 1 are digested with various restriction endonucleases in various combinations and then the resulting DNA fragments cloned into M13 phage vectors to form single stranded DNA templates. A universal primer is used to sequence the sense and nonsense strands. Rather than relying on the sequencing results obtained from sequencing the entire length of the fragments with a single chain termination procedure, in the longer fragments additional synthetically produced primers are used to initiate the chain termination procedure from intermediate locations along the lengths of the fragments. By this process, both strands of the cDNA clones shown in FIG. 1 are sequenced in overlapping fashion, thereby serving to redundantly confirm the sequences.

It is to be understood that rather than employing the chain-termination technique outlined above, other konw methods may be utilized to sequence the IL-2 receptor gene without departing from the spirit or scope of the present invention. For instance, the chemical degradation method of Maxam and Gilbert as set forth in 74 *Proc. Nat'l Acad. Sci.* (*USA*) 560 (1977) can be used.

*Expression Of Functional IL-2 Receptor From cDNA Clones*

Figure 3A:
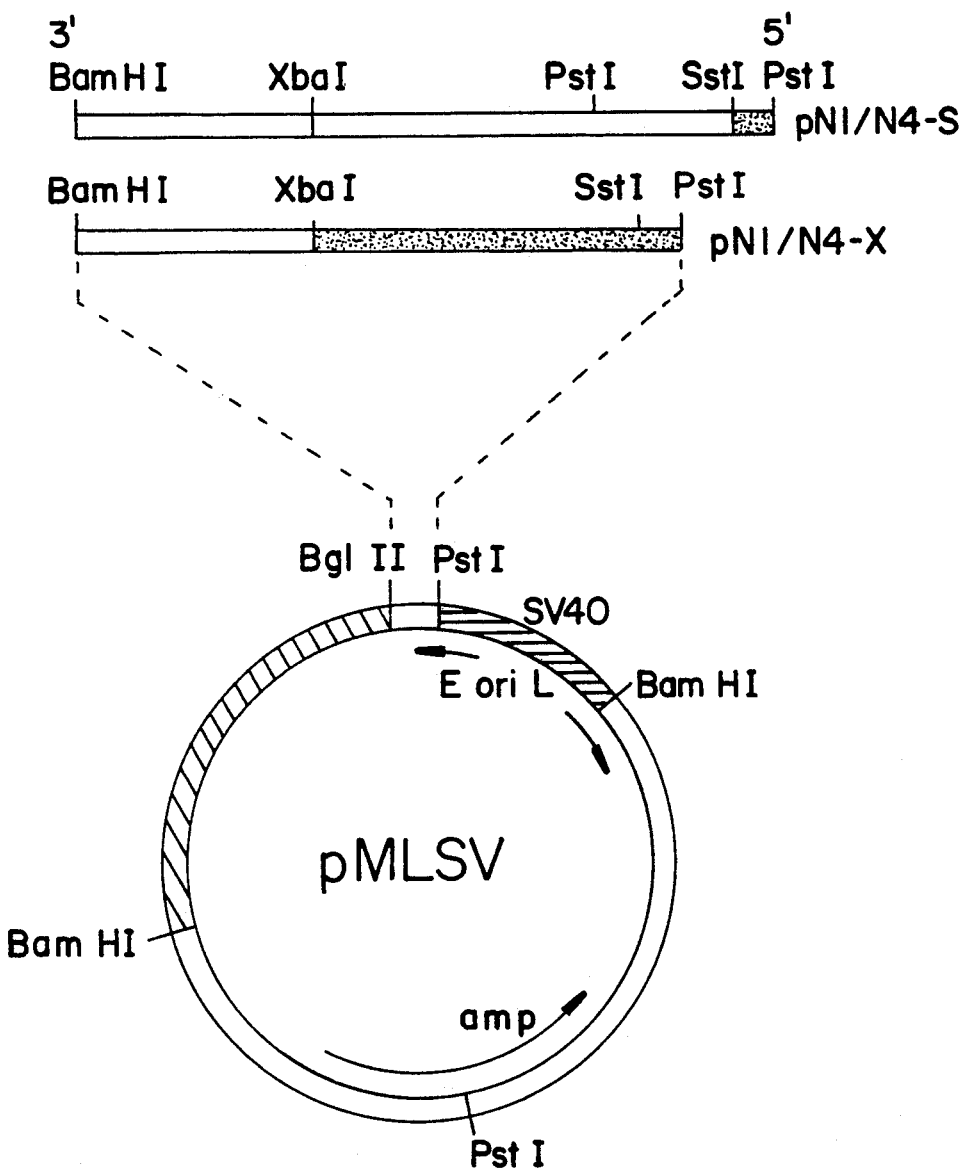
FIG. 3A illustrates the strategy employed to clone the coding regions of the N4 and N1 fragments in plasmid vectors used to transfect mammalian cells to determine whether one or both cDNA clones would encode a functional IL-2 receptor.

To determine whether the cDNA coding regions of the N1 or N4 clones could encode a functional IL-2 receptor, the clones are expressed in mammalian cells. Hybrid cDNA fragments containing the coding regions of the N4 and N1 clones are inserted into a plasmid vector derived in part from simian virus 40 ("SV40"). The genome of this virus consists of a single, small, covalently closed circular DNA molecule whose entire nucleotide sequence has been determined, Fiers et al., 237 *Nature*, (*London*) 113–120 (1978), and Reddy et al., 200 *Science* 494–502 (1978). The two constructed vectors, designated as pMLSV-N1/N4-S and pMLSV-N1/N4-X, having the coding regions of the N4 and N1 clones, respectively, are illustrated in FIG. 3A.

The above-delineated vectors are transfected into mammalian cells. After subsequent incubation, the cells are harvested and assayed for expression of mature IL-2 receptor by their ability to bind to labeled IL-2 or the labeled 2A3-A1H monoclonal antibody directed against the IL-2 receptor. Labeled 2A3-A1H monoclonal antibody may be prepared as described above. IL-2 may be prepared by established methods, such as set forth in U.S. Pat. No. 4,401,756, and in Urdal et al., 296 *J. Chromatog.* 171 (1984) and then radiolabeled, for instance by use of a radioiodination reagent such as Enzymobead ® (BioRad Laboratories, Richmond, Calif.). As shown in sections B and C of FIG. 3, the mammalian cells transfected with the pN1/N4-S vector specifically bound to both IL-2 and the 2A3-A1H monoclonal antibody. However, neither pN1/N4-X or mock-transfected cells (prepared as a control) specifically bound to IL-2 or the 2A3 monoclonal antibody. Since the pN1/N4-S vector contained the coding region of the N4 clone, this indicated that this clone contains the gene coding for the functional IL-2 receptor protein, whereas the N1 clone does not.

The processes and products of the present invention are further illustrated by the following examples.

EXAMPLE 1

Preparation of IL-2 Receptor Containing Extracts From Malignant Cell Line

Hut-102 cells in a concentration of $2 \times 10^5$ cells per ml were cultured in 100–500 ml volumes in various plastic culture flasks or bottles (Falcon Plastics, Oxnard, Calif.) in RPMI-1640 medium. The medium was supplemented with 10% FCS, 2 mM glutamine, 100 U/ml penicillin and 100 ug/ml streptomycin. Since the HUT-102 cells have been reported to produce human T-cell leukemia virus (HTLV-1), work with this cell line was performed in a P-3 isolation facility.

The cells were cultured for 3–5 days in a humidified atmosphere of 5% $CO_2$ in air. After this period of time, viable cells were harvested by centrifugation and washed three times in PBS. Thereafter, the cell pellet was suspended in a volume that is three times the volume of the cell pellet in a solution composed of PBS containing 1% (w/v) Triton X-100 detergent and 2 mM PMSF. This mixture was kept on ice and periodically vortexed for 30 minutes. The extract was then centrifuged at $20,000 \times g$ for 20 minutes to remove nuclei and insoluable debris. The cell extract, as thus prepared, was then stored at $-70°$ C. until used.

EXAMPLE 2

Preparation of IL-2 Receptor Containing Extracts From Lectin Activated Normal Cells Human peripheral blood mononuclear cells were prepared by Ficoll-Hypaque density gradient centrifugation as described by Boyum, supra. The resulting cells were incubated separately in 100-mm plastic petri dishes in 8% FCS at a concentration of $2-5 \times 10^6$ per ml. The adherent cells were recovered with a rubber policeman after removing nonadherent cells with three media washes. The E$^-$ adherent cells together with the E$^+$ nonadherent cells in a ratio of 1:25 were placed in bulk culture in 75-cm$^2$ flasks at a concentration of about $1-2 \times 10^6$ cells/ml in RPMI-1640 medium supplemented with 10% FCS, 100 U/ml penicillin and 100 ug/ml streptomycin. Activation was accomplished with 1% (v/v) PHA (Difco Laboratories, Detroit, Mich.). The cultures were incubated at 37° C. in an humified atmosphere of 5% $CO_2$ in air. Aliquots containing approximately $1-2 \times 10^7$ cells were removed at various times for analysis of cell surface IL-2 receptors.

Cells were harvested by centrifugation approximately 72 hours after mitogen stimulation, and washed three times with PBS. The resulting cell pellet was suspended in a volume three times the volume of the pellet in a solution composed of PBS containing 1% (w/v) Triton X-100 detergent and 2 mM PMSF. The resulting mixture was kept on ice with periodic vortexing for 30 minutes. Thereafter, the extract was centrifuged at $20,000 \times g$ for 20 minutes to remove nuclei and insoluable debris. The resulting cell extracts were stored at $-70°$ C. centrigrade until used.

EXAMPLE 3

Production of Monoclonal Antibody To IL-2 Receptor

Female BALB/c (Jackson Laboratories, Bar Harbor, Me.) of ages of from 8–12 weeks were immunized intradermally in the hind legs with $10^7$ PHA/PBL. Prior to immunization, the PHA/PBL cells were prepared as an emulsion by mixing these cells with 0.4 ml of complete Freund's adjuvant (Difco Laboratories). After the initial immunization, the mice were rechallenged weekly for four weeks with $10^7$ PHA/PBA in incomplete Freund's adjuvant.

Periodically, serum from the mice was collected and tested individually for binding to PHA/PBL by ELISA, in a manner well known in the art. The animals found to have the highest response were given an additional intravenous injection of $10^7$ PHA/PBL in PBS. Four days later, the animals were sacrificed by cervical dislocation. The spleens of the animals were harvested and single cell suspensions prepared therefrom. The spleen cells were cultured in medium.

Fusion was achieved by mixing approximately $20 \times 10^6$ spleen cells with approximately $10 \times 10^6$ NS-1 murine myeloma cells in a 50 ml conical centrifuge tube. The cell mixture was pelleted by centrifugation for 5 minutes at $200 \times g$, and then the supernate removed by aspiration. The centrifuge tube with its intact cell pellet was transferred into a 37° C. water bath. Then polyethylene glycol 15 w (Eastman, Inc.) (50% (w/v) in RPMI-1640 was added to the cell pellet in dropwise manner at a ratio of 1 ml of PEG/$1.6 \times 10^8$ spleen cells. Thereafter, one volume of RPMI-1640 and 10 volumes RPMI 1640 containing 15% FCS and 1 mM pyruvate were slowly added during gentle stirring. Then, the cell suspension was centrifuged at $200 \times$ g for 5 minutes and the supernate discarded to complete the fusion process.

The hybrid cells were selected by resuspending the resulting cell pellet in Click's medium containing 15% FCS and 100 mM sodium pyrvate. The unfused myeloma driver cells (NS-1), double NS-1 hybrids, unfused spleen cells and double spleen cell hybrids were prevented from proliferation by the addition to the medium of approximately 13.6 mg/L of hypoxanthane, 0.176 mg/L aminopterin and 3.88 mg/L of thymidine. The suspension was then divided into 200 ul aliquots in flat-bottom microliter plates (No. 3596, Costar Inc., Cambridge, Mass.). The cultures were maintained at approximately 37° in a humified atmosphere of 5% $CO_2$ in air.

After 10 days of culture, a 100 ul aliquot of supernate was removed from each viable culture and tested in an ELISA assay for binding to PHA/PBL (IL-2 receptor positive) or PBL (IL-2 receptor negative). Hybrids which demonstrate significant binding to PHA/PBL and little or no binding to PBL were transferred to 1 ml cultures and gradually weaned to HAT-free media. These hybrids were subcloned by limiting dilution cultures. Through this process, applicants have identified one particular hybrid clone, designated as 2A3-A1H, which significantly inhibits both mitogen and antigen induced proliferation of human PBL. Samples of this cell line are on deposit with the American Type Culture Collection ("ATCC"), Rockville, Md., under accession No. HB 8555. The 2A3-A1H monoclonal antibody has been characterized as of the $\gamma_1 K$ isotype that exhibits a very high affinity to the human IL-2 receptor. This antibody inhibits the binding of IL-2 to its receptor and is antagonistic of IL-2 action.

EXAMPLE 4

In Vivo Production of Hybridoma Cells Producing Monoclonal Anti-IL-2 Receptor Antibodies Anti-IL-2 receptor antibody was produced in high concentration in vivo by intraperitoneal injection of BALB/c mice with approximately $1-10 \times 10^6$ hybridoma cells. One week prior to hybridoma cell injection, recipient BALB/c mice were given approximately 1.0 ml of pristane intraperitoneally as an ascites inducing irritant. From 8 to 14 days after hybridoma injection, intraperitoneal ascites were collected and each volume of fluid is mixed with 0.9 volume of 45% saturated ammonium sulfate and stirred overnight. The precipitate was separated by centrifugation and redissolved in phosphate buffer (0.05M), pH 6.8. Residual ammonium sulfate was removed by dialysis against the same buffer.

The protein solution was then passed over a 5 ml bed volume DE-52 column (Whatman, Clifton, N.J.) and the fronting peak of protein was pooled. The pooled fractions were dialyzed against 0.02M sodium borate, 0.1M sodium NaCl, pH 8.5, ("BBS") and then applied to a 2.6×90 cm ACA-34 (LKB, Bromma, Sweden) gel filtration column previously equilibrated in the same buffer. The fractions corresponding to IgG were collected and pooled. Yields typically were in the range of 3 mg IgG/ml of ascites.

EXAMPLE 5

Purification of IL-2 Receptor By Affinity Chromotography

Cell extracts from normal and malignant cells produced by the procedures of Examples 2 and 3 were concentrated by affinity chromatography technique employing an initial gel column having control antibody for removing protein that might nonspecifically bind to mouse IgG and a second column having 2A3-A1H antibody bound thereto. The control antibody used in the initial column was secreted by the myeloma cell line MOPC-21. This antibody is of the same isotype as the 2A3-A1H antibody and is readily available.

To prepare the columns, purified 2A3-A1H and MOPC-21 antibodies were coupled to Affi-gel-10 (BioRad, Richmond, Calif.) according to the manufacturer's instructions. Equal volumes of moist Affi-gel-10 and antibody (3-5 mg/ml) in PBS were mixed together and incubated overnight at 4° C. Thereafter, unreacted sites on the Affi-gel-10 were blocked by addition of 100 ul of 1M glycine ethyl ester per ml of gel. Applicants found that the antibody-coupled gel routinely contained from 3 to 4 mg of antibody per ml of gel.

Because the 2A3-A1H antibody exhibits such an extremely high affinity for the IL-2 receptor, the receptor yield from the chromatography columns was improved by employing columns prepared with a mixture of MOPC-21 and 2A3-A1H antibody. A total of 3 to 4 mg IgG was still coupled per ml of gel, but only 10-30% of the IgG is composed of 2A3-A1H. The column having both MOPC-21 and 2A3-A1H antibody bound thereto will be referred to as the "2A3-A1H" column.

Prior to use, each gel was washed extensively with PBS and RIPA buffer. The MOPC-21 and 2A3-A1H gel columns were poured in 3 ml syringes that have their open ends closed with a cork and tubing, thereby to enable the columns to be run in either direction. The cell extracts, as prepared in Examples 1 and 2 above, were first applied to the MOPC-21 column at a flow rate of 0.1 ml/min at 4° C. to remove proteins the non-specifically bind to the mouse IgG. This absorption was repeated once more and then the flow-through from the MOPC-21 column is twice applied to the 2A3-A1H column.

The 2A3-A1H column was then washed with 10 column volumes of PBS-1% Triton X-100, 10 column volumes of RIPA buffer and lastly, 10 column volumes of PBS-1% Triton X-100. Thereafter, the receptor was eluted from the column with 6M guanidine hydrochloride ("GuHCl") and 0.5% Triton X-100. Eluate fractions in 1.2 ml volume were collected and each fraction was dialyzed against 3M GuHCl in 0.5% Triton X-100 for four hours. This was followed by dialysis against 1.5M GuHCl in 0.5% Triton X-100. Final dialysis was performed against PBS containing 0.5% Triton X-100. Aliquots at each stage of the purification were saved for analysis of: biological activity by the above-described soluble receptor assays; protein concentration by fluorescamine assay with bovine serum albumin as a standard, as is well known in the art; and, protein heterogeneity by polyacrylamide gel electrophoresis with the protein being detected by silver staining, as also described above. From these assays, the IL-2 receptor from the HUT-102 cells was found to have a specific activity of approximately 2,000 fm receptor/ug protein. The specific activity from the PHA-PBL cells was somewhat less.

EXAMPLE 6

Reversed Phase High Performance Liquid Chromatography

The active fractions obtained in Example 5 were pooled for use as the starting material for the HPLC process. These fractions were pumped directly onto a 3.9 mm times 15 cm Vydac C-4 column, which had been previously equilibrated with 0.1 percent TFA in water, at a flow rate of about 1 ml/min with a Waters M-45 A solvent pump (Waters Associates, Millford, Me.). The loaded column was initially washed with 0.1% TFA to remove nonbound components until the absorbence at 214 nanometers as detected with a Waters Model 441 absorbence detector drops to base line. Elution of bound proteins was accomplished with a linear gradiant of 0-95% acetonitrile in 0.1 percent TFA (v/v) at a rate of 1% per minute. The IL-2 receptor protein was found to elute off the column in the 50 to 55% acetonitrile fractions.

One minute fractions were collected (1 ml) and 50 ul aliquots were removed from each fraction for analysis by polyacrylamide gel electrophoresis followed by silver staining. This technique resulted in the separation of a single band of protein at a molecular weight of 55,000 daltons for the HUT-102 receptor molecule. The PHA-PBL receptor molecule, which eluted at the same position on the HPLC as the HUT-102 receptor molecule, exhibited a single band of protein having a molecular weight of 600,000 daltons.

Aliquots in 50 ul volumes were also removed from the minute fractions for biological assay. The aliquots were dried under vacuum in the presence of 50 ug BSA. The dried residue was dissolved in PBS-2% Triton X-100 for analysis by the soluble receptor assay techniques discussed above. This assay indicated that the IL-2 from HUT-102 receptor had been purified from 1.26 fmole receptor/ug in protein the cell lysate starting material to approximately 21,000 fmole receptor/ug protein after the HPLC purification step. This equates to an increase in purification of the IL-2 receptor of about 16,670 times. The specific activity of the PHA-BPL receptor after the HPLC purification step was found to be approximately 5,000 fmole receptor/ug protein. It is clear from the single protein bands which resulted from the polyacrylamide gel electrophoresis and silver staining of the fractions collected after HPLC, and also from the specific activities of the fractions analyzed by the soluble receptor assays, essential homogeneity of the IL-2 receptor molecule was achieved.

EXAMPLE 7

Protein Sequencing

Purified IL-2 receptor from Example 6 was dried under vacuum to a final volume of approximately 100 ul and then subjected to automated amino terminal Edman degration using an Applied Biosystems Model 470A protein sequencer. Fractions from the sequencing cycles were evaporated to dryness and then resuspended in acetonitrile/$H_2O$ (50:50) before injection into an HPLC column for residue identification.

By the above process, the amino-terminal amino acid sequence for the IL-2 receptor from both the HUT-102 and PHA-PBL cells were found to be the same. The first 15 residues of the N-terminal portion of the IL-2 receptor molecule was determined to be composed of the following sequence: Glu-Leu-Cys-Asp-Asp-Asp-Pro-Pro-Glu-Ile-Pro-His-Ala-Thr-Phe. This amino acid sequence was compared with known protein sequences contained in the National Biomedical Research Foundation protein data base "SEARCH" (January, 1984), and was not significantly homologous to any protein sequence contained in this data base.

EXAMPLE 8

Preparation of Polyadenylated mRNA

Hut-102 cells at a concentration of approximately $2 \times 10^5$ cells/ml were cultured in 100–500 ml volumes in RPMI-1640 medium supplemented with 10% FCS (v/v), 2 mM glutamine, 100 U/ml penicillin and 100 ug/ml streptomycin. The cells were cultured for 3–5 days in a humidified atmosphere of 5% $CO_2$ in air. After this period of time, viable cells were harvested by centrifugation.

Total RNA was extracted from the Hut-102 cells by the method as described by Chirgwin et al., supra. In this procedure guanidinium thiocyanate was used to denature the cellular protein including the RNase at a rate that exceeds the rate of RNA hydrolysis by RNase. The mRNA was removed from the cellular protein by ultracentrifugation through a dense cushion of cesium chloride.

Thereafter, polyadenylated mRNA was separated from the extracted protein on an oligo (dT)-cellulose chromatography column using the method disclosed by Maniatis et al., supra at 197. Briefly, the column was prepared with application buffer composed of 20 mM Tris-Cl (pH 7.6), 0.5M NaCl, 1 mM ethylene diamine tetraacetate ("EDTA") and 0.1% sodium dodecyl sulfate ("SDS"). The pellet was dissolved in water and application buffer and then loaded onto the column. The nonadsorbed material was removed by initial washings with application buffer followed by additional washings with application buffer containing 0.1M NaCl. The retained polyadenylated mRNA was removed with buffers of reduced ionic strength composed of 10 mM Tris-C;l (pH 7.5), 1 mM EDTA and 0.05% SDS. The eluted polyadenylated mRNA was precipitated at $-20°$ C. with 1/10 volume sodium acetate (3M, pH 5.2) and 2.2 volumes of ethanol. After elution of the polyadenylated mRNA from the oligo (dT)-cellulose column, the integrity of the polyadenylated mRNA was confirmed by electrophoresis through agarose gels as detailed in Maniatis et al., supra at 199.

EXAMPLE 9

Construction of cDNA Library

A library of double-stranded cDNA corresponding to the mRNA was prepared from the purified mRNA in Example 8 by employing the procedure detailed by Maniatis et al., supra at 229. Oligo-dT was hybridized to the polyadenylated tail of the mRNA to serve as the primer for the reverse transcription of the first cDNA strand. The enzyne avian myeloblastosis virus ("AMV") reverse transcriptase was employed to synthesize the first DNA strand by using the mRNA as a template. This procedure resulted in a hairpin loop being formed at the 3' end of the initial cDNA strand. The hairpin loop served as an integral primer for the second cDNA strand. After the mRNA strand was degraded with NaOH, the second cDNA strand was synthesized with DNA polymerase I. The hairpin was then removed with nuclease S1 to produce doublestranded cDNA molecules.

The double-stranded cDNA was fractionated into size classes by Sephacryl S-400 column chromatography and monitored by alkaline agarose electrophoresis using end-labeled fragments of pBR322 DNA as molecular-weight markers. Strands having a length of less than 500 bp were culled out to avoid needless cloning of these undersized cDNA fractions.

The double-stranded cDNA fractions, as prepared above, were inserted into the Pst I site of the pBR322 plasmid. The double-stranded cDNA was tailed with poly (dC) at its 3' ends. The plasmid pBR322 was digested with Pst I endonuclease and then tailed with poly (dG) at its 3' ends. The tailed plasmid DNA and the tailed cDNA were annealed in annealing buffer (0.1M NaCl, 10 mM Tris-Cl (pH 7.8) and 10 mM ETDA) to form novel recombinant plasmids.

The recombinant plasmids were transformed into E. coli strain MM294 by using the procedure of Hanahan, supra in which the E. coli cells were prepared by growth in elevated levels of $Mg^{2+}$. The transformation hosts were plated and then transformants are identified by use of tetracycline as a phenotypic identifier. By use of this technique, applicants obtained approximately $2 \times 10^6$ independent transformants.

EXAMPLE 10

Preparation of Synthetic Oligonucleotide Screening Probes

Synthetic oligonucleotides were employed as a probe in screening the cDNA library prepared as set forth above in Example 9. The probes were composed of the following compositions: 5' G-G-$c^T$-G-G-G-T-C-G-T-C-G-T-C-A-C-A 3'. These oligonucleotide probes were chemically synthesized by triester method using the well known techniques of Sood et al., supra and Hirose et al., supra.

After chemical synthesis had been completed, the 5' ends of the oligonucleotide probes were labeled with $^{32}$P. To facilitate labeling, the 5' ends of the oligonucleotide were synthesized with OH termini, thereby eliminating the phosphatese treatment which typically must be employed when labeling DNA fragments. The labeling protocol included adding 1 ul of the synthetic oligonucleotides to 16 ul of $^{32}$P-ATP (7000 Ci/mM), 1 microliter ("ul") (10 U) of T4 polynucleotide kinase and 2 ul of 10×kinase buffer I. The 10×kinase buffer I was composed of 0.5M Tris-Cl (pH 7.6), 0.1M $MgCl_2$, 50 mM dithiothreitol, 1 mM spermidine and 1 mM ETDA. The reaction was carried out at 37° C. for 30 minutes, and thereafter the synthesized oligonucleotides were extracted with phenol/chloroform. The labeled probes were separated from unlabeled oligonucleotides by chromatography on or centrifugation through Sephadex G-50 columns.

EXAMPLE 11

Screening of cDNA Library

To facilitate initial screening of the cDNA library prepared in Example 9 above, the transformed bacteria cultures were grouped into pools each having approximately 5,000 different clones. Plasmid DNA was removed from samples of the host bacteria by the well known alkaline lysis method, for instance as described by Ish-Horowicz and Burke, 9 *Nucl. Acids Res.*, 2989 (1981).

The isolated plasmids were separated into two fragments. This was accomplished by initially digesting the plasmids to completion with Pvu II and Hind III. The plasmids were redissolved in 20 ul of 1×Hind III buffer (7 mM Tris, (pH 7.4), 7 mM magnesium chloride, 60 mM NaCl) and then 1 ul of Pvu II and 1 ul of Hind III restriction endonucleases were added. This mixture was incubated at 37° C. for two hours.

Next, the plasmid digests were fractionated by electrophoresis through 0.8% agarose gel wtih markers of appropriate size. The agarose gel was blotted onto nitrocellulose filter using the well known method described by Southern, supra. After the transfer process, the filter was air dried and baked for two hours at approximately 80° C. under a vacuum to bind the DNA fragments to the nitrocellulose.

The bound DNA was next hybridized with the labeled oligonucleotide probes. Briefly, the baked nitrocellulose was presoaked in 6×saline sodium citrate ("SSC") (20 X SSC is composed of 175.3 g of NaCl and 88.2 g of sodium citrate in 800 ml of $H_2O$, with pH adjusted to 7.0 with 10N NaOH) and then incubated at 50° C. for 2-4 hours in prehybridization buffer composed of 6×SSC, 0.5% NP40 detergent, 0.1% sarcosyl, 5×Denhardt's solution (0.02% Ficoll, 0.02% polyvinyl pyrrolidone, 0.02% BSA) and 100 ug/ml denatured salmon sperm DNA (Sigma Type III, sodium salt). The filter was then incubated overnight at 50° C. with the $^{32}$P-labeled oligonucleotide probe ($10^6$ cpm/ul) (from Example 10) in hybridizing solution as above. After overnight hybridization, the filter was washed extensively with 6×SSC at room temperature and then for 5 minutes at 50° C. with 6×SSC. After air drying, the filter was subjected to autoradiography at −70° C.

From the autoradiography, applicants found several pools of transformants generating hybridizing bands. The appropriate pools of the transformants were plated out and then used in direct bacterial colony hybridization on nitrocellulose paper with the labeled oligonucleotide probe under the same hybridizing conditions as above. By this process, two positive colonies were identified.

EXAMPLE 12

Restriction Enzyme Mapping of Screened cDNA

Plasmids, designated as N4 and N1, were prepared from the identified positive colony by the procedures set forth in Example 9. Samples of the N4 and N1 plasmids transformed into *E. coli* strain MM294 are on deposit with the ATCC, under Accession Nos. 39752 and 39751, respectively. Thereafter, the N4 and N1 plasmids were analyzed by restriction enzyme mapping using the standard method developed by Smith and Birnstiel, supra, involving partial digestion of end-labeled fragments of the linearized DNA. The DNA fragments were labeled at their 5' termini with $^{32}$P-phosphoryl groups using polynucleotide kinase and $^{32}$P-ATP. The labeled DNA strands were then cleaved asymmetrically with a suitable restriction enzyme to provide two fragments, each labeled at only one of its ends. These labeled fragments were isolated by gel electrophoresis. Each of the two fragments was partially digested by appropriate restriction enzymes. Although a large spectrum of digestion fragments were produced, the labeled fragments formed a simple overlapping series each having a common labeled terminus. These fragments were fractionated by gel electrophoresis and then examined by autoradiography. The locations of the fragments on the gel correspond directly to the order of the restriction sites along the plasmid DNA.

By this procedure, applicants partially mapped the restriction sites, as shown in FIG. 1, of the N4 and N1 plasmid cDNAs in the region of the IL-2 receptor gene.

EXAMPLE 13

Sequencing of Screened cDNA

The DNA fragments shown in FIG. 1 were initially partially sequenced by the dideoxy chain termination method. From the sequencing results, applicants confirmed that the N4 DNA fragment shown in FIG. 1 contains the gene coding for the IL-2 receptor, with the N-terminus of the mature IL-2 receptor protein being located at the Sst I site of the DNA fragment shown in FIG. 1.

Thereafter, the portions of the N4 and N1 clones from the 5' terminals to the Xba I restriction sites were sequenced by the chain termination protocol essentially as described in the Amersham Handbook, supra, with the variations set forth below. The N4 and N1 clones were digested with Pst I, Sst I and Xba I restriction endonucleases in various combinations and then the resulting DNA fragments were cloned into strains mp18 and mp19 of the M13 single-stranded filamentous phage vector (Amersham, Arlington Heights, Ill.). The mp18 and mp19 phage vectors, as set forth in Norrander et al. supra, contain the following unique cloning sites: Hind III; Sph I; Pst I; Sal I; Acc I; Hinc II; Xba I; BamHI; Xma I; Sma I; Kpn I; Sst I; and, EcoRI. The composition of the mp18 and mp19 vectors are identical, with the exception that the order of the above-identified restriction sites are reversed in the mp19 vector so that both strands of a DNA segment may be conveniently sequenced with the two vectors. The mp18 and mp19 vectors, with fragments of the N4 and N1 clones inserted therein, were used to transform *E. coli* JM103 and JM105 of the strain K12 (Bethesda Research Laboratories, Bethesda, Md.) to produce relicate single-stranded DNA templates containing single-stranded inserts of the sense and antisense strands.

The synthetic universal primer: 5'-CCCAGTCAC-GACGTT-3' (P-L Biochemicals, Milwaukie, Wis.), was annealed to the single-strand DNA templates and used to prime DNA synthesis as described above at page 23. Thereafter, the extension fragments were size-separated by gel electrophoresis and autoradiographed from which the nucleotide sequences of the fragments were deduced.

An additional primer was employed to prime synthesis from an intermediate location along the sense strands of the N4 and N1 clones. A primer having the composition: 5'-GTGACACCTCAACCTGA-3', corresponds to nucleotides 262 through 278 (FIG. 2). The composition of this primer strand was established from the sequencing information previously obtained by the sequencing of the N4 and N1 clones from their 5' termini with the universal primer. An additional synthetic primer of the composition: 5'-TGTGACGAGGCAG-GAAG-3' (corresponding to nucleotides 613 through 629 in FIG. 2) was used in sequencing the antisense strands between the Xba I and Sst I sites of the N4 and N1 clones. By the above "walk down" method, the strands of the N4 and N1 clones were sequenced from their 5' terminals to their Xba I sites in an overlapping, redundant manner thereby confirming the nucleotide sequence of these clones. It is to be understood that other synthetic primers could have been employed to initiate chain extensions from other locations along the N4 and N1 clones, without departing from the scope of the present invention.

Deoxyadenosine 5' (alpha-[$^{35}$S] thio) triphosphate (hereinafter "dATP [alpha-$^{35}$S]") was used as the radioactive label in the dideoxy sequencing reactions. Also, rather than using the gel set forth at page 36 of the Amersham Handbook, a 6% polyacrylamide gel was employed (6% polyacrylmide gel, 0.4 mm thick, containing 7M, urea 100 mM Tris borate (pH 8.1), and 2 mM EDTA).

As noted above, the nucleotide sequences of the N4 and N1 clones from their 5' terminals to the Xba I sites are illustrated in FIG. 2. This segment of DNA was found to include the coding regions of the clones. The nucleotides are numbered from the position of the initiator methionine codon. The corresponding amino acids, as determined by the nucleotide sequence and by protein sequence analysis, are set forth above the appropriate codons. The amino acid composition of the IL-2 receptor gene extends from the mature NH$_2$-terminus of the IL-2 receptor molecule, i.e., the Glu residue, as marked with a star in FIG. 2 (from which the numbering of the amino acid residues begins), to the Ile residue (No. 251) immediately preceding the termination codon TAG. Various restriction enzyme cleaving sites are also indicated in FIG. 2. The portions of the coding regions of the N4 and N1 clones in FIG. 2 are illustrated as boxed regions in FIG. 1, with the solid box portions indicating substantially corresponding portions of the clones and the open box portion depicting the 216 base pair sequence only present in the N4 clone.

EXAMPLE 14

Expression of Mature IL-2 Receptor In Mammalian Cells

The coding regions of the N4 and N1 clones were inserted into a plasmid vector for transfection of mammalian cells to ascertain whether either coding region encodes a functional IL-2 receptor. The transfected cells were assayed for expression of IL-2 receptor by their ability to bind either labeled IL-2 or a labeled monoclonal antibody directed against the IL-2 receptor, i.e., 2A3-A1H monoclonal antibody. Hybrid cDNAs containing the coding regions of the N4 and N1 clones (illustrated in FIG. 3A), designated as pN1/N4-S and pN1/N4-X, respectively, were inserted into the pMLSV phage vector, shown as a circle, to produce the plasmids pMLSV-N1/N4S and pMLSV-N1/N4X, respectively.

The pMLSV vector was derived principally from SV40 whose genome consists of a single, small covalently closed DNA molecule that has been entirely sequenced, Fiers et al., supra, and Reddy et al., supra. The pMLSV vector is composed of four parts, including the stippled box portion shown in FIG. 3A which contains the control region of the SV40 plasmid (including the origin of DNA replication, enhancer elements and early and late promoters) (SV40 coordinates 5107-208). This vector portion was originally derived from the psV2-dhfr vector as a Hind III-Pvu II fragment, Subramani et al., 1 *Mol. Cell Biol.* 854–864 (1981) and Lebowitz and Weissman, 87 *Current Topics in Microbiology and Immunology* 43 (1979). For use in the pMLSV plasmid, the Pvu II site was converted into a BamHI site and the Hind III site converted to Xba I site.

Downstream from the early promoter, the pMLSV vector includes a synthetic polylinker of the composition:

```
5'-CTAGAAGCTTGGTACCAGCTGCAGATCTC
3'-TTCGAACCATGGTCGACGTCTAGAG

GAGAATTCATCGAT-3'
          CTCTTAAGTAGCTAGATC-5'.
```

This polylinker has Xba I cohesive termini and contains the following restriction sites: Hind III; Kpn I; Pvu II; Pst I; Bgl II; Xho I; EcoRI; Cla I; and, Xba I. The hatched box portion of the plasmid contains the SV40 small t antigen donor and acceptor splice junctions (SV40 coordinates 4035-4656) and the SV40 polyadenylation signal (SV40 coordinates 2469-2706), originally derived from the pSV2-dhfr plasmid as a Bgl II-BamHI fragment, Subramani, supra. The Bgl II site was converted to a Xba I site for correspondence with the adjacent terminal of the synthetic polymer.

The long thin line portion of the pMLSV plasmid is derived from the plasmid pML2d, a derivative of plasmid pBR322, that lacks sequences inhibitory to DNA replication in mammalian cells, Sarver et al., 79 *Proc. Natl. Acad. Sci. (USA)* 7147–7151 (1982); and, Luskey and Botchan, 293 *Nature* 79–81 (1981).

Because it is known that the presence of dG-dC tails at the 5' end of a cDNA insert can inhibit its expression in mammalian cells (for instance, see Riedel et al., 3 *EMBO Journal* 1477 (1984)), hybrid cDNAs were constructed by combining portions of the N4 and N1 cDNA clones with the sequences derived from the N4 clone shown as open boxes and the sequences derived from the N1 clone shown as solid boxes in FIG. 3A. As illustrated, the pN1/N4S hybrid fragment includes the portion of the N4 clone from the BamHI site to the 5' Sst I site to which is attached the 5' Pst I-Sst I fragment from the N1 clone, and thus contains the coding region of the N4 clone. The pN1/N4X hybrid cDNA contains a 5' Pst I-Xba I fragment from the N1 clone and a Xba I-BamHI fragment from the N4 clone, and thus contains the coding region of the N1 clone. It will be appreciated that both of the hybrid cDNAs take advantage of the "natural" Pst I site in the 5' prime noncoding region of the N1 clone that lacks tails. The pN1/N4-S and pN1/N4-X hybrid cDNAs having Pst I and BamHI cohesive ends were inserted into the Pst I and Bgl II sites of the pMLSV plasmid by standard techniques, for instance, as detailed in Maniatis et al., supra, to form plasmid vectors pMLSV-N1/N4-S and pMLSV-N1/N4-X, respectively. The pMLSV-N1/N4-S plasmid vector has been deposited with the ATCC under Accession No. 39890.

The plasmids as prepared above were transfected into COS-7 monkey kidney cells (ATCC, Rockville, Md.) by standard techniques, for instance, by essentially using the procedures described by Lauthman and Magnusson, 11 *Nucl. Acid Res.* 1295 (1983). Monolayers of COS-7 cells ($10^6$ cells per 10 cm plate) were washed twice with Tris-buffered saline ("TBS") and exposed to 10 ug of hybrid pMLSV-pN1/N4-S or pMLSV-pN1/N4-X DNA per plate in 1 ml TBS containing 500 ug/ml DEAE-Dextran (molecular weight $5 \times 10^5$; Sigma Chemical Company, St. Louis, Mo.) for 30 minutes at room temperature. The cells were washed once more with TBS and fed with growth medium (Dubecco's Modified Eagle's Medium with 10% (v/v) fetal bovine serum) containing 100 uM chloroquine (St. Louis, Mo.). After incubation for five hours at 37° C., the medium was replaced by growth medium without chloroquine. The cells were then incubated at 37° C. for 48 hours, after which time they were harvested by scraping.

The transfected COS-7 cells were screened for IL-2 receptor expression by ascertaining the ability of the cells to bind to $^{125}$I-labeled anti-IL-2 receptor antibody 2A3-A1H (FIG. 3B) and also to $^{125}$I-labeled IL-2 (FIG. 3C). The 2A3-A1H monoclonal antibody was prepared and radiolabeled to a specific activity of $9.8 \times 10^{14}$ cpm/mM, as described above.

Purified IL-2 was radiolabeled using the Enzymobead radioiodination reagent (BioRad Laboratories, Richmond, Calif.) essentially by the manufacturer's specifications. Fifty ul aliquotes of IL-2 ($5 \times 10^6$ units) in 65% acetonitrile and TFA (pH 2.1) were combined with 50 ul of 0.2M sodium phosphate (pH 7.2) and then the acetonitrile evaporated under nitrogen. Fifty ul of Enzymobead reagent, 10 ul of $^{125}$I (1 mCi) and 10 ug of 2.5% Beta-D-glucose (BioRad Laboratories, Richmond, Calif.) were added and then the mixture incubated at 25° C. for 10 minutes. Twenty ul of 25 mM sodium azide and 10 ul of sodium metabisulfite (5 mg/ml) were then added, and after 5 minutes of incubation at 25° C., iodinated IL-2 was separated from unbound $^{125}$I by chromatography on a 2 ml column of Sephadex G-25 equilibrated in 0.05M sodium phosphate (pH 7.2) containing 0.1% v/v BSA and eluted with this same buffer. Based on an initial biologic specific activity for IL-2 of $1 \times 10^6$ units/ug protein, the radiolabeled preparation had an estimated specific activity of $1 \times 10^{15}$ cpm/mM.

The binding assays were performed as described in Dower et al., 132 *J. Immunol.* 751 (1984). COS-7 cells ($1.2 \times 10^6$) were incubated with either $5 \times 10^{-9}$M $^{125}$I-2A3-A1H monoclonal antibody or $1.3 \times 10^{-8}$M $^{125}$I-IL-2 in a final volume of 150 ul of binding medium for 30 minutes at 37° C. Nonspecific binding was measured in the presence of 1000-fold molar excess of unlabeled 2A3-A1H monoclonal antibody or 150-fold molar excess of unlabeled IL-2. Replicate 70 ul aliquots of the above incubation mixtures were centrifuged through phthalate oil to separate the $^{125}$I bound to COS-7 cells from the unbound cells ($^{125}$I labeled IL-2 or 2A3-A1H).

The results of the $^{125}$I binding assay are set forth in panels B and C of FIG. 3. As shown, only the pMLSV-N1/N4-S transfected COS-7 cells bound to the labeled IL-2 and labeled 2A3-A1H monoclonal antibody. Neither the pMLSV-N1/N4-X transfected COS-7 cells or the mock-transfected COS-7 control cells showed any specific binding of IL-2 or the monoclonal anti-IL-2 receptor antibody. Since only the pMLSV-N1/N4-S hybrid contains the N4 coding region, the functional IL-2 receptor protein is encoded thereby.

As will be apparent to those skilled in the art to which the invention is addressed, the present invention may be carried out by using cell lines, culture media, culture media additives, culture conditions, assays, antibodies, purification restriction mapping and sequencing techniques, and chromatography columns other than those specifically discussed above without departing from the spirit or essential characteristic of the invention. The particular materials and processes described above are therefore to be considered in all respects as illustrative and not restrictive. The scope of the present invention is as set forth in the appended claims rather than being limited to the examples of the methods and procedures set forth in the foregoing description.

The embodiments of the invention in which an exclusive property or privilege is claimed are defined as follows:

1. A homogeneous interleukin 2 receptor protein, precipitatable by monoclonal antibody 2A3-A1H, that has a molecular weight by SDS polyacrylamide gel electrophoresis of about 55,000 to 60,000 daltons and that has a specific activity from approximately 5,000 to approximately 21,000 femtomoles of interleukin 2 receptor per microgram of protein, wherein said protein comprises an N-terminal sequence Glu-Leu-Cys-Asp-Asp-Asp-Pro-Pro-Glu-Ile.

2. A homogeneous interleukin 2 receptor protein according to claim 1, obtained by cloning and expression of a DNA sequence that hybriding under stringent conditions to a synthetic oligonucleotide probe corresponding to a portion of the amino acid sequence of an interleukin 2 receptor.

3. A homogeneous interleukin 2 receptor protein according to claim 2, wherein said DNA sequence is expressed in a mammalian cell.

* * * * *